United States Patent [19]
Subbiah

[11] Patent Number: 5,365,456
[45] Date of Patent: Nov. 15, 1994

[54] METHOD FOR MODELLING THE ELECTRON DENSITY OF A CRYSTAL

[75] Inventor: Subramanian Subbiah, Woodside, Calif.

[73] Assignee: The Board of Trustees of the Leland Stanford University, Palo Alto, Calif.

[21] Appl. No.: 831,258

[22] Filed: Jan. 30, 1992

Related U.S. Application Data

[63] Continuation-in-part of Ser. No. 648,788, Jan. 30, 1991, Pat. No. 5,200,910.

[51] Int. Cl.$^5$ .............................................. G06F 15/20
[52] U.S. Cl. .................................. 364/499; 364/554; 364/555
[58] Field of Search ............... 364/499, 554, 578, 555, 364/496, 498, 560

[56] References Cited

U.S. PATENT DOCUMENTS 4,855,931  8/1989  Saunders ............................. 364/499
5,200,910  4/1993  Subbiah ............................... 364/499

OTHER PUBLICATIONS

Barton et al.; "Microstructural Characterization"; IEEE Transactions on Magnetics, vol. 25, No. 2, Mar. 1989.
Khachaturyan et al., *The Thermodynamic Approach to the Structure Analysis of Crystals*, Acta Cryst. (1981) A37:742-754.
S. V. Semenovskaya, *Statistical Mechanics Approach to the Structure Determination of a Crystal*, Acta Cryst. (1985) A41:268-273.
S. Subbiah, *Adrift in Patterson Space*, A Proposal for the Qualifying Exam in the Harvard Ph.D. Program in Biophysics (1986).
S. Subbiah, *Low Resolution Real-Space Envelopes: An Approach to the Ab Initio Macromolecular Phase Problem*, Science, 252, 128-133, Apr. 5, 1991.

*Primary Examiner*—Ellis B. Ramirez
*Attorney, Agent, or Firm*—Hickman & Beyer

[57] ABSTRACT

A method for modelling the electron density distribution of a macromolecule in a defined asymmetric unit of a crystal lattice having locations of uniformly diffracting electron density includes the steps of: producing an initial distribution of scattering bodies with a asymmetric unit having the same dimensions as the defined asymmetric unit; calculating scattering amplitudes of the initial distribution and determining the correlation between the calculated scattering amplitudes and the normalized amplitudes; moving at least one of the scattering bodies within the asymmetric unit to create a modified distribution; calculating scattering amplitudes and phases of the modified distribution and determining the correlation between the calculated amplitudes and producing a final distribution of scattering bodies by repeating moving and calculating steps until the correlation between the calculated scattering amplitudes and the normalized amplitudes is effectively maximized, the final distribution of scattering bodies defining the electron density of the crystal.

24 Claims, 12 Drawing Sheets

Microfiche Appendix Included
(4 Microfiche, 240 Pages)

METHOD FOR MODELLING THE ELECTRON DENSITY OF A CRYSTAL

This application is a continuation in part of U.S. application Ser. No. 648,788 (now U.S. Pat. No. 5,200,910), filed Jan. 30, 1991 which is incorporated herein by reference for all purposes.

MICROFICHE APPENDIX

This specification includes microfiche Appendix A having 4 sheets with 240 frames.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present invention relates to the fields of crystallographic methods and apparatus for determining the three-dimensional structure of macromolecules by crystallography or electron microscopy.

Under special conditions, molecules condense from solution into a highly-ordered crystalline lattice, which is defined by a unit cell, the smallest repeating volume of the crystalline array. The contents of such a cell can interact with and diffract certain electromagnetic and particle waves (e.g., X-rays, neutron beams, electron beams etc.). Due to the symmetry of the lattice, the diffracted waves interact to create a diffraction pattern. By measuring the diffraction pattern, crystallographers attempt to reconstruct the three dimensional structure of the atoms in the crystal.

A crystal lattice is defined by the symmetry of its unit cell and any structural motifs the unit cell contains. For example, there are 230 possible symmetry groups for an arbitrary crystal lattice, and each symmetry group may have an arbitrary dimension that depends on the molecules making up the lattice. Biological macromolecules, however, have asymmetric centers and are limited to 65 of the 230 symmetry groups. See Cantor et al., Biophysical Chemistry, Vol. III, W. H. Freeman & Company (1980), which is incorporated herein by reference for all purposes.

A crystal lattice interacts with electromagnetic or particle waves, such as X-rays or electron beams respectively, that have a wavelength with the same order of magnitude as the spacing between atoms in the unit cell. The diffracted waves are measured as an array of spots on a detection surface positioned adjacent the crystal. Each spot has a three-dimensional position, hkl, and an intensity, I(hkl), both of which are used to reconstruct the three-dimensional electron density of the crystal with the so-called Electron Density Equation:

$$\rho(x,y,z) = \frac{1}{V} \sum_{h,k,l=-\infty}^{\infty} F(h,k,l)\exp[-2\pi i(hx + ky + lz)]$$

where $\rho(x,y,z)$ is the electron density at the position (xyz) in the unit cell of the crystal, V is the volume of the unit cell, and F(h,k,l) is the structure factor of detected spot located at point (h,k,l) on the detector surface. As expressed above, the Electron Density Equation states that the three-dimensional electron density of unit cell is the Fourier transform of the structure factors. Thus, in theory, if the structure factors are known for a sufficient number of spots in the detection space, then the three-dimensional electron density of the unit cell could be calculated using the Electron Density Equation.

A number of problems exist, in actual practice, however. The Electron Density Equation requires knowledge of the structure factors, F(h,k,l), which are generally complex numbers that consist of both an amplitude and a phase. The amplitude of a structure factor, F(h,k,l), is simply the square root of the experimentally measured intensity, I'(h,k,l). The phase of each structure factor, on the other hand, is not known and cannot be measured directly in a diffraction experiment. Nor can it derived directly for macromolecules. Without the phase of each structure factor, determination of the three-dimensional structure of most large structures by the use of the Electron Density Equation is impossible except for special cases.

Theoretical methods are exemplified by the Direct Method and the Patterson Method or their extensions, as well as the maximum entropy method or the use of simulated annealing in both reciprocal and Patterson space. These methods calculate the phases directly from the measured intensities of the diffacted waves and allow routine computer solutions for molecules having typically less than approximately 100 non-hydrogen atoms. (As is known in the art of crystallography, hydrogen atoms contribute little to the diffraction process.) For structures having more than 100 non-hydrogen atoms, such as proteins, peptides, DNA, RNA, virus particles, etc., such direct methods become impractical and, in most cases, impossible. Fortunately, experimental methods, such as Multiple Isomorphous Replacement and Anomalous Scattering, exist to aid in the determination of these phases.

Multiple Isomorphous Replacement is based on the observation that the absolute position and, therefore, the phase of the structure factor of a heavy atom incorporated into an otherwise unmodified crystal lattice can be determined. With this knowledge, the phase of each structure factor in the derivative is determined relative to that of the heavy atom. Except for crystals having centrosymmetric symmetry, at least two heavy metal derivatives are required to unambiguously determine the phase of a structure factor. Furthermore, Multiple Isomorphous Replacement requires that each heavy metal derivative does not otherwise change the structure of the molecule, or distort the unit cell of the crystal.

Other experimental techniques, used in conjunction with Multiple Isomorphous Replacement allow the crystallographer to forego analysis of some heavy metal derivatives. One such technique, Anomalous Scattering, is based on the observation that particular heavy atoms scatter radiation of different wavelengths significantly differently. With this technique, one heavy metal derivative studied at two wavelengths yields data equivalent to two heavy atom derivatives studied at one wavelength.

Other techniques completely circumvent the preparation and study of heavy metal derivatives.

Molecular replacement, as the name suggests, uses a molecule having a known structure as a starting point to model the structure of the unknown crystalline sample.

This technique is based on the principle that two molecules that have similar structures and similar orientations and positions in the unit cell diffract similarly. Effective use of this technique requires that the structures of the known and unknown molecules be highly homologous.

Molecular replacement involves positioning the known structure in the unit cell in same location and orientation as the unknown structure. Difficulty in using this technique arises because the result is critically dependent on the exact position of the known structure. Slight variations in either the same location or orientation of the known structure often results in complete failure. Once positioned, the atoms of the known structure in the unit cell are used in the so-called Structure Factor Equation to calculate the structure factors that would result from a hypothetical diffraction experiment. The Structure Factor Equation takes the form:

$$F(h,k,l) = \sum_{j=1}^{N} f_j \exp[2\pi i(hx_j + ky_j + lz_j)]$$

where F(hkl) is the structure factor of the molecule at the point (hkl) on the detector surface, $f_j$ is the atomic structure factor (that is, it represents the scattering properties of the individual atom), N is the number of non-hydrogen atoms, and $x_j$, $y_j$, $z_j$ are the factional coordinates of atom j in the unit cell. The structure factor calculated is generally a complex number containing both the amplitude and phase data for the molecular replacement model at each point (hkl) on the detector surface. These calculated phases are used, in turn, with the experimental amplitudes measured for the unknown structure to calculate an approximate electron distribution. By refinement techniques, this approximate structure can be fine-tuned to yield a more accurate and often higher resolution structure.

The molecular replacement technique requires knowledge of the number of molecules, and the orientation and position of each molecule within the unit cell. Initially the electron density calculated from the phases from the molecular replacement model and experimental amplitudes closely resembles the electron density of the model. Only after refinement of the initial structure will the success or failure of the method be apparent. For instance, failure occurs if the initial structure fails to converge (as represented by a correlation value) or if the refined structure diverges from the structure of the model during the refinement process. In cases where the unknown structure is a substrate or intermediate bound to a protein, molecular replacement's success is evident when the result is a structure whose only difference is added electron density that represents the protein-bound molecule. The determination of such structures is important in the area of pharmaceutical drug testing where the structure of protein-bound drugs and intermediates yield important information about binding and mechanism. Similarly, new mutants of a protein or variations of protein-bound inhibitors are well suited for molecular replacement, as are structures of the same molecule that have crystallized in different symmetry groups.

Molecular Replacement is not always effective, however. Determination of the number of copies of the model in the asymmetric unit and the correct location and orientation of each copy is critical and time consuming, since ideally one samples all rotational and translational degrees of freedom in the asymmetric unit to determine the correct set of parameters.

Multiple Isomorphous Replacement, Molecular Replacement, and their related techniques, do not work for all cases, however, and there exists a need for a simplified, efficient methods to determine the structure of crystalline molecules. The present invention fulfills these and other needs.

SUMMARY OF THE INVENTION

The present invention produces a model of the electron density distribution of a macromolecule in a defined asymmetric unit of a crystal lattice in multi-step methods. These methods are simple and rapid ways of modelling the electron density of a crystal, without the need to determine the phases of the reflection data. According to one aspect of the invention, data collected from an X-ray diffraction experiment of a crystal lattice are inputted into a computer, and are converted into normalized amplitudes. The crystal lattice has a defined asymmetric unit having locations of uniformly diffracting electron density. An initial distribution of scattering bodies is produced within a asymmetric unit that has the same dimensions as the defined asymmetric unit of the crystal lattice. The scattering amplitudes and phases of the initial distribution are then calculated, and the correlation between the calculated scattering amplitudes and the normalized amplitudes is calculated to determine the fit between the two data sets. At least one of the scattering bodies within the unit cell is moved to create a modified distribution, the scattering amplitudes of this modified distribution are calculated, and the correlation between the calculated amplitudes and the normalized values is recalculated. A final distribution of scattering bodies is produced by repeating the steps of moving at least one of the scattering bodies to create a modified distribution and determining the correlation between the calculated amplitudes and the normalized values, until the correlation between the calculated scattering amplitudes and the normalized amplitudes is effectively maximized. This final distribution of scattering bodies defines the electron density of the crystal.

In a preferred embodiment of the present invention, a scattering body is moved a predetermined distance. In another preferred embodiment, the method includes additional steps. The final distribution is refined by at least one refining step that reduces the predetermined distance that a scattering body is moved. At least one of the scattering bodies is moved by the reduced distance within the asymmetric unit to modify the distribution, the scattering amplitudes of this modified distribution are calculated, and the correlation between the calculated amplitudes and the normalized amplitudes is determined. Finally, the refining step produces a final distribution of scattering bodies by repeating steps of moving at least one scattering body and calculating the correlation between the calculated amplitudes of the distribution and the normalized values, until the correlation is maximized. The final distribution of scattering bodies define a refined electron density of the crystal.

Other preferred embodiments include one or more of the following features. The refining step is repeated with decreasing move distances, until the move distance is reduced to a predetermined final value. The scattering bodies are translated in a random translation direction, and the random translation direction is randomly selected from predefined translation directions, which are parallel to the axes defined by the crystal lattice unit cell.

In another preferred embodiment, the step of determining the fit between the calculated amplitudes of scattering bodies and the normalized amplitudes consists of calculating a correlation coefficient between the calculated amplitudes and the normalized values.

In another aspect of the invention, a model of the electron density distribution of a macromolecule in a defined asymmetric unit of a crystal lattice having locations of uniformly diffracting electron density is produced by inputing data collected from an X-ray diffraction experiment into the computer. A plurality of scattering bodies is randomly distributed in another asymmetric unit having substantially the same dimensions as the defined asymmetric unit. The plurality of scattering bodies is then moved into a final distribution, whereby the scattering amplitudes of the final distribution have a maximum fit with amplitudes from the data. This final distribution defines the electron density distribution of the macromolecule in the defined unit cell.

BRIEF DESCRIPTION OF THE DRAWINGS

FIG. 4b is a stereoscopic view the alpha carbon backbone of Elastase superimposed on the final distribution of scattering bodies of FIG. 4a;

FIG. 11 is a graph showing the behavior of the Pearson correlation coefficient, r, during the condensing protocol.

DESCRIPTION OF THE PREFERRED EMBODIMENT

Table of contents

Figure 1A:
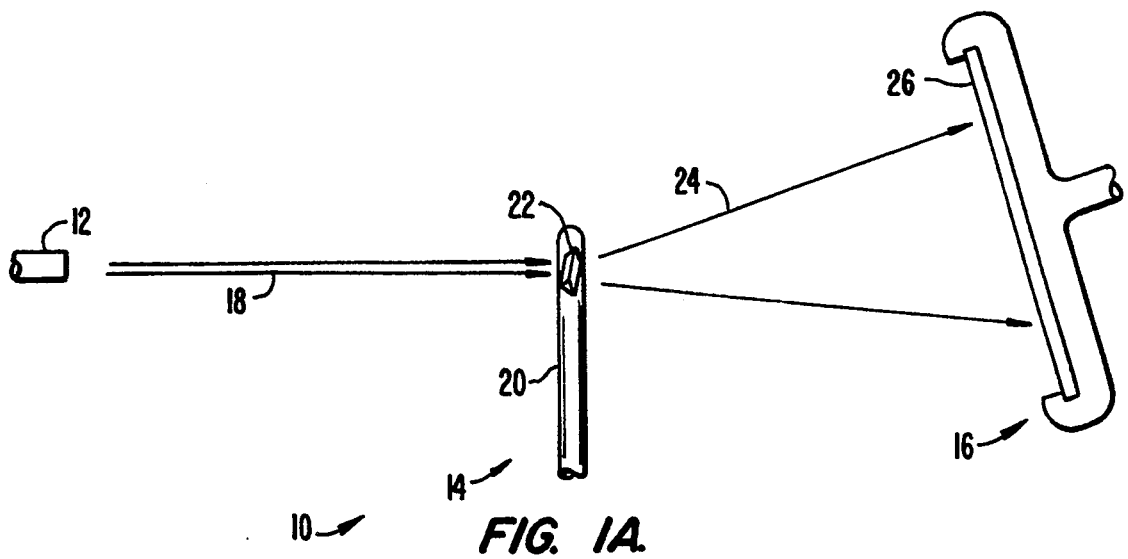
FIG. 1 is a schematic drawing of an X-ray diffractometer.
FIG. 1b is a schematic representation of the detection plate of FIG. 1.
FIG. 1c is a block diagram illustrating the computer hardware to which the invention may be applied.

I. Overview of the method
II. Modes of carrying out the invention
III. Data Collection and Manipulation
IV. Initial Distribution of Scattering Bodies
V. Calculation of the correlation coefficient
VI. Condensing Protocol
VII. Examples
VIII. Other Embodiments The present invention will be described by providing details of each step involved in the modelling.

I. Overview

When macromolecules crystallize, solvent typically occupies large portions of the crystal lattice including regions in the interior as well as space exterior to the macromolecular envelope. The bulk of the solvent incorporated with the macromolecule is fluid and consists of randomly oriented molecules that do not diffract X-rays, electron beams, neutron beams, and the like. The portion of the unit cell occupied with the macromolecule is termed the "positive image," while the portion occupied with solvent is termed the "negative image." The term "macromolecular envelope" denotes the surface of the macromolecule and may be determined at different resolutions. Thus, a high resolution macromolecular envelope includes many detailed features of the macromolecular surface, such as location of side chains, clefts, etc. Conversely, a low resolution envelope includes few detailed features and provides details about the general shape of the macromolecule.

The term "macromolecule" includes, but is not limited to the following: biological macromolecules such as proteins, peptides, RNA, DNA, complexes of peptides and nucleic acids, virus particles, organelles, and the like; organic molecules such as organic polymers, plastics; inorganic molecules such as zeolites; and other large molecular structures. Although the term "protein" is used below in conjunction with the description of illustrative embodiments, the method is fully suited for structure determination of other macromolecules that crystallize into a unit cell having solvent space.

In a preferred embodiment, an initial distribution of scattering bodies is rearranged into the final distribution that represents the negative image of the crystal. That is, the scattering bodies in the final distribution are located in the portion of the crystal occupied with solvent rather than the portion occupied with the macromolecule. The electron density distribution of the macromolecule is modelled as the portion of unit cell that is substantially devoid of scattering bodies.

In other preferred embodiments, however, the initial distribution rearranges into a final distribution representative of the positive image. In such embodiments, the final distribution of scattering bodies is located in the portion of the crystal occupied by the macromolecule. The electron density distribution is then modelled based on this final distribution of scattering bodies.

II. Modes of carrying out the Invention

The invention methods include different steps: collecting diffraction data; inputing experimental crystallographic data into a computer which is used to perform the method; distributing scattering bodies in a corresponding asymmetric unit; calculating scattering data from this distribution; determining the correlation between the experimental and calculated scattering data; moving at least one of the scatterers; calculating the new scattering data from this new distribution; determining the correlation between the new scattering data and the experimental data; and producing a final distribution by repeating the moving, calculating and correlating steps until the correlation between the experimental and calculated data is maximized.

III. Data Collection and Manipulation

Collection of diffraction data from scattered waves is well known in the art of crystallography. Referring to FIG. 1, a diffractometer 10 (also known as an X-ray set) for use with the present invention includes a source of X-rays 12, a sample holder 14, and a detection apparatus 16. X-ray source 12 produces a collimated beam 18 of X-rays having a relatively narrow cross section and is typically a mercury flash tube or copper cathode or rotating anode that produces X-rays having a narrow and well-defined wavelength spectrum.

In other preferred embodiments, alternate forms of radiation and radiation sources are used. For example, an alternate source of X-rays, such as a tunable X-ray source (e.g., radiation from a synchrotron or other source that emits X-rays of different wavelengths) is preferred for use with techniques such as Anomalous Scattering or Multiple Wavelength Scattering. Alternate forms of radiation include electron beams (e.g., those typically used in electron microscopy), neutron beams (e.g., those typically used in neutron beam diffraction), and the like.

Sample holder 14 consists of a capillary tube 20 having a crystallized sample 22 located within its lumen. Capillary tube 20 and crystallized sample 22 are positioned in the path of collimated X-ray beam 18. X-rays 24 diffracted by the crystal impinge a detection apparatus 16 that is positioned generally opposite X-ray source 12 and that consists of a detector surface 26 mounted on an arm 28. Detection surface 26 takes on many shapes, such as a two-dimensional disk, a three-dimensional cylindrical surface, and the like, and is adapted to record the position and intensity of diffracted X-rays 24. Examples of suitable detection surfaces for use in the present invention include photographic film, gas chamber or multi-wire area detectors, CCD channel plates, image plates, diffractometers including precession cameras, and the like. In many apparatus, e.g., a precession camera, the rotation of sample holder 14 and detector surface 26 are coupled during the diffraction experiment to accumulate data corresponding to an entire plane in reciprocal space.

Figure 1B:
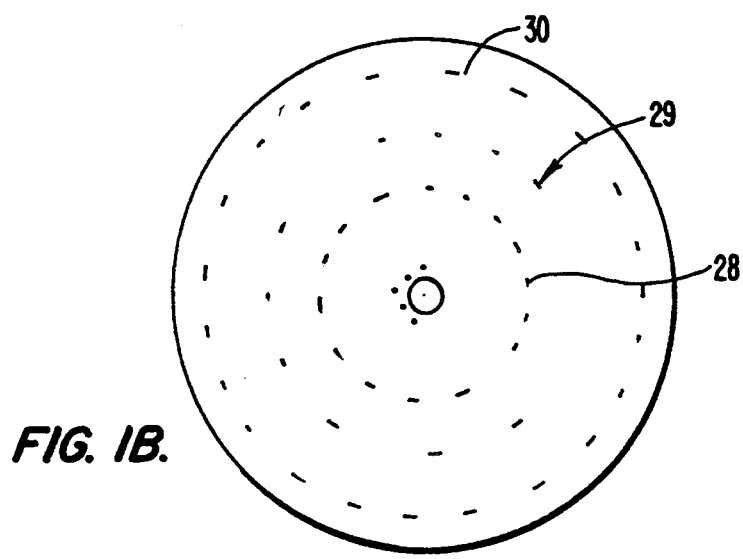

Referring now to FIG. 1a, detector surface 26 after exposure to diffracted X-rays consists of an array of spots that each have a position, (hkl), and an intensity, I(hkl). The data form an array having a circular boundary 30 that represents the high resolution limit of the diffraction experiment. Data representing low resolution features of the crystal are located near the center of the circular array while data representing the high resolution features are near the outer edge. For example, data lying within the circle defined by circle 28 represent lower resolution features of the crystal (e.g., down to 10 Å), while data lying between circles 29 and 30 represent features of higher resolution (e.g., between 2 Å and 5 Å).

During a diffraction experiment, data collection typically involves accumulation of a large number of data points, often over 10,000. After accumulation on an appropriate detection surface the position and intensity of each data point is measured, as is known in the art of crystallography, and the data are put into a computer for storage and further processing. In a preferred embodiment, the computer is a digital computer such a VAX 8550, produced by Digital Equipment Corporation of Maynard, Mass. Other computers of varying computational power are also suitable: supercomputers, multiprocessor computers, mainframe computers, work stations, personal computers, and the like. Exemplary computers for use with the present invention include computers produced by Cray Research, Digital Equipment Corporation, Thinking Machines, Data General, International Business Machines, Apple Computer, Sun Computers, and Silicon Graphics. In other embodiments special duty computers are used. For example, an appropriate digital computer incorporated into a diffractometer is suitable for performing the invention method.

Figure 1C:
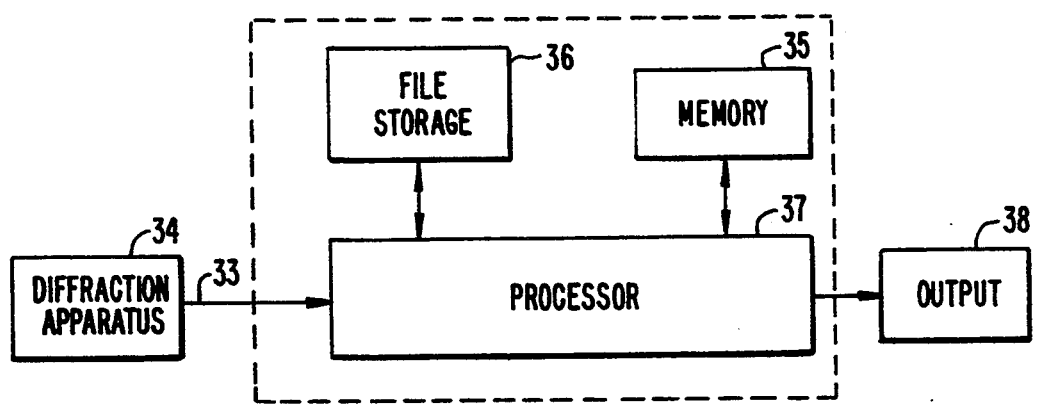

Referring now to FIG. 1c, a computer 32 used in conjunction with the present invention include an interface 33 to receive data from a diffraction apparatus 34, memory 35 (e.g., RAM), file storage 36 (e.g., magnetic disk or tape) to store the data, and a CPU 37 to process the data. In preferred embodiments, the computer further includes an output device 38, such as a printer, plotter, or graphics display, that allows the resulting electron density of the crystal to be displayed graphically. Typical graphic displays are produced by Evans and Sutherland. Computer coding (Fortran) that has been used to implement the present invention is attached hereto as appendix A. The main routine (phasolm6-Oa.f) is compiled together with the subroutines presented in Appendix A.

As previously mentioned, the crystallographic symmetry and dimensions of the unit cell and asymmetric unit are determined directly from the data (see Blundell and Johnson "Protein Crystallography" Academic Press, N.Y. 1976, which is incorporated herein by reference for all purposes). The unit cell is the smallest portion of the crystal lattice that repeats upon operation of a translation. Thus, the crystal is composed of a repeating array of unit cells in three dimensions, and determining the electron density of the unit cell is equivalent to determining the electron density of the crystal lattice. In most space-groups, the unit cell has multiple copies of the crystallized macromolecule, and may have internal symmetries, such as a plane of reflection, an n-fold rotation axis, etc., termed "crystallographic" symmetries. Subspaces of the unit cell that are related by such crystallographic symmetries, are termed "asymmetric units." Determining the electron density of the asymmetric unit is also equivalent to determining the electron density of the crystal lattice, by first applying the appropriate symmetry operations to reconstruct the unit cell and then translating the unit cell. As used herein, the term "asymmetric unit" refers to portions of the unit crystal lattice that can be repeated by translations, rotations, or combination thereof, to reconstruct the crystal lattice. Thus, for some crystals, the asymmetric unit is the same as the unit cell (when there is no known crystallographic symmetry). In other crystals for example, the asymmetric unit may be half of the unit cell. Once the symmetry and dimensions of the asymmetric unit are determined, as is known in the art, the experimental data are converted from unsealed F-values into a form convenient for use in the method of the present invention.

In a preferred embodiment, a portion of the experimental data are converted into normalized structure-factor magnitudes (i.e., E-values) that are conventionally used in Direct Methods (See Karle, Acta Crystal. 1989, vol. A45, pp. 765–781, which is hereby incorporated by reference for all purposes). As used herein, "portion" is used to indicate a subset or the whole of the experimental data, since some cases require conversion of the entire data set, while others require conversion of a subset. While F-values represent scattering by atoms that have a finite electron distribution, normalized E-values represent scattering by bodies that have no spatial distribution and have a simple scattering cross-section. Thus, this conversion models the crystal as an array of point scatterers rather than atoms. Alternatively, the accumulated data is converted into properly scaled F-values, as described in Blundell and Johnson. The use of properly scaled F-values or normalized E-values depends on the details of the calculations. In a preferred embodiment, E-values are used in conjunction with high resolution data. With data having resolutions lower than approximately 8 Å, however, either F-values or normalized E-values are used (with a corresponding change in the Electron Density and Structure Factor Equation as is well known in the art) with no substantial difference in the results. In ensuing discussions, therefore, properly scaled F-values and normalized E-values are used interchangeably at lower resolutions unless otherwise specified, and are collectively referred to as "experimental data."

Once diffraction data are collected and converted to properly scaled F-values or normalized E-values, and the crystallographic symmetry and dimensions of the asymmetric unit have been determined, the electron density of the crystal is modelled by a distribution of point-scatterers.

V. Initial Distribution of the Scattering Bodies

To model the electron density of the crystal, an initial distribution of scattering bodies is created and allowed to condense (that is, to rearrange) into a final distribution, with two constraints. The first constraint is based on a "physical" packing of the scattering bodies, and the second is based on correlating the scattering resulting from the distribution of scattering bodies to the experimental data.

In other embodiments, a third constraint, the "compactness" constraint, is additionally employed. Since proteins at low-resolution are generally compact and globular in shape, a final distribution of scattering bodies that fills the macromolecular positive image will by necessity have its individual scatterers close to each other. The compactness constraint exploits this property by dictating that scatterers increasingly "cluster together" during the condensation process.

The initial distribution of scattering bodies is created by placing a plurality of scatterers into an asymmetric unit having the same symmetry and dimensions as the asymmetric unit of the crystal lattice. The scattering bodies are hypothetical objects used to model the electron density of the crystal and have physical characteristics such as a radius and scattering cross-section. As described below, the number and properties of the these scatterers depend on the properties of the asymmetric unit of the crystal.

Like physical objects, no part of more than one scattering body can occupy the same space in the asymmetric unit; in other words, two scattering bodies can approach each other until their surfaces touch. Without this physical limitation, the scattering bodies may condense into the same small region in the asymmetric unit. The scattering bodies have an outer surface, and can be of many shapes and sizes. In a preferred embodiment, a scattering body is a sphere, ellipsoid, cube, tetrahedron, etc. In more preferred embodiment, the scattering bodies are spherical in shape and have a predefined radius, r, although the radius of the scattering body may vary, as described more fully below. In a most preferred embodiment, each scatterer has a radius of 1.5.

Although each scattering body is preferably spherical and has a radius, each is treated as a point scatterer having a scattering factor of unity. Such a choice is made for the convenience of computation, since application of the Structure Factor Equation is easier to compute for point scatterers. In other preferred embodiments, however, the scatterers have scattering profiles that approximate the spatial distribution of a real atom, such as a Gaussian profile or a Normal profile. The Structure Factor Equation becomes more complex, however, and the computation time increases upon increasing the complexity of these scattering profiles.

Point scattering bodies cannot provide a phase description of the macromolecule to a resolution better than their inter-sphere collision distance (e.g., 3 Å of spheres having a 1.5 Å radius). Application of the present invention to solving structures at resolutions higher than 3 Å requires scatterers having smaller radii, as discussed below.

The number of scatterers distributed within the asymmetric unit depends on many factors, such as the radii of the scatterers, the number of non-hydrogen atoms in the asymmetric unit, the solvent fraction of the asymmetric unit (or, equivalently, the expected packing fraction of the macromolecule), and the resolution and number of reflections experimentally collected.

The number and physical characteristics of the scattering bodies that optimally satisfy the expected protein packing fraction are chosen. Optimal packing of the scatterers allows the distribution of scatterers to have mobility within the solvent portion of the asymmetric unit during the condensation process. That is, the scatterers have enough free space in which to move.

The number of spherical scattering bodies of a radius, r, required to maximally fill the volume occupied by the solvent incorporated into the asymmetric unit in a particular crystal, $N_{max}$, is determined. Once this maximum number is known, allowance is made for mobility within the distribution of scatterers.

Biological macromolecules generally crystallize with a large amount of solvent incorporated into the asymmetric unit, and it is possible to estimate the percentage of solvent content with reasonable accuracy, as is known in the art. In the case of proteins, enzymes, polymeric nucleic acids etc., the primary sequence may be used to estimate the volume of the protein. Typical algorithms for calculating the volume of amino acids and polypeptides are well known in the art. In a preferred embodiment, an average value the solvent fraction of about 0.4 (i.e., 40% of the unit cell volume) is used as an estimate for the solvent fraction of the asymmetric unit.

For a plurality of spheres having the same radius, the theoretical value for the maximal random packing fraction is about 0.6. That is, spheres randomly packed to maximize their density will fill 0.6 (i.e., 60% of the volume). This value, combined with the average solvent content of the asymmetric unit (i.e., 40%), provides the number of spherical bodies needed to maximally fill the solvent space as:

$$N_{max} = (0.6)(0.4) \frac{V_{asymmetric\ unit}}{V_{sphere}} = 0.24 \frac{V_{asymmetric\ unit}}{\left(\frac{4}{3}\pi r^3\right)}$$

where r is the radius of each sphere. This value is unrealistic for the invention method, however, since it requires that the spheres lie in an extremely tightly, packed lattice. Even if there were no Fourier constraints to be satisfied, the requirement that the distribution of scattering bodies be mobile and fluid requires that the optimum number of scattering bodies be significantly smaller than the maximum number. Additionally, there are limitations imposed by the Fourier constraints that further decrease the number of scatterers, as described below.

In a preferred embodiment, the optimal number of scattering bodies, $N_{hs}$, is between (0.01) $V_{asymmetric\ unit}/V_{sphere}$ = and (0.15) $V_{asymmetric\ unit}/V_{sphere}$. In a more preferred embodiment, the number of scattering bodies is between (0.04) $V_{asymmetric\ unit}/V_{sphere}$ and (0.08) $V_{asymmetric\ unit}/V_{sphere}$.

In the case of protein or peptide crystallography, when the packing fraction of the peptide is in the range P=0.5 to 0.6, the number of alpha carbons ($C_\alpha$) of a typical protein, $N_{\alpha\alpha}$, is approximately 1;5 times greater than the value for $N_{hs}$. Thus, in a preferred embodiment, $N_{hs} = 0.67\ N_{c\alpha}$.

Once the number of scatterers is determined, as described above, the asymmetric unit is randomly filled with the appropriate number (e.g., $N_{hs} = 0.67\ N_{ca}$ for typical proteins) of scattering bodies of a predetermined radius, for example 1.5 Å. As described above, the centers of any two 1.5 Å radius spheres cannot approach closer than 3 Å.

In a preferred embodiment, the initial distribution of the spheres is produced by positioning a first scattering body within a volume having the same dimensions and symmetry as the asymmetric unit of the crystal. Subsequently, a second scattering body is positioned in the asymmetric unit under the constraint that its center is at least 3 Å away from the center of the other body. Placement of scattering bodies continues until the asymmetric unit is filled with the desired number of scattering bodies.

Many methods are suitable for the positioning of each scattering body. In a preferred embodiment, each scattering body is placed at a random position, subject to the constraint that the centers of no two spheres are closer than 3 Å. In another preferred embodiment, each scattering body is placed at a regular position in the asymmetric unit, such as a grid point of a rectilinear array, subject to the same constraint as described above.

Before further calculations are performed, the unit cell is reconstructed from the asymmetric unit by the appropriate symmetry operations, as described above.

V. Calculation of the Correlation between the Calculate Amplitudes and the Experimental Data Once the initial distribution of the scattering bodies is determined, the Fourier amplitudes of this distribution are calculated by a trigonometric summation using the Structure Factor Equation. In a preferred embodiment, the following equation is used:

$$F(h,k,l) = \sum_{j=1}^{N} f_j \exp[2\pi i(hx_j + ky_j + lz_j)]$$

In other preferred embodiments, other methods for calculating the Fourier amplitudes are used. Suitable methods include, for example, Fast Fourier Transfer methods (See Press et al. Numerical Recipes in C: The Art of Scientific Computing, Cambridge University Press, 1988, incorporated herein by reference for all purposes.)

The calculated Fourier amplitudes and the experimental data are then correlated to determine the fit between the positions of the scattering bodies in the initial distribution and the positions of the atoms in the crystal. Many methods for determining the correlation between two sets of data exist. In a preferred embodiment, the Pearson correlation coefficient, r, is used. The Pearson coefficient takes the form:

$$r = \frac{\Sigma(|E_e| - <|E_e|>)(E_c - <|E_c|>)}{\sqrt{\Sigma(|E_e| - <|E_e|>)^2 \Sigma(|E_c| - <|E_c|>)^2}}$$

where E is the experimental data, $E_c$ is calculated amplitude and the summations are taken over all experimental data points. To maximize the fit between data, the value of the Pearson coefficient is maximized.

In another preferred embodiment the crystallographic correlation, R, is used to correlate the data sets (See, Blundell and Johnson. This correlation exhibits behavior opposite of the Pearson Coefficient: a closer correlation between the experimental data and the calculated amplitudes results in a smaller value of R. Thus, to maximize the fit between the two data sets, R is minimized. Other methods of correlating the two data sets are well known and will be apparent to those skilled in the art.

The choice of resolution, K, at which the two data sets are correlated depends primarily on two conditions. First, the resolution cannot exceed the inter-collision distance of the scattering bodies 3 Å. Second, there should be sufficient over-determinacy; that is, the number of experimental data points should be larger than the number of scattering bodies. One can use more of the experimental data, but for a low resolution image such data makes little difference. For instance, when the crystallized molecule has a large unit cell, data having a resolution of approximately 7 to 10 Å generally provide sufficient over-determinacy. For smaller unit cells, however, sufficient over-determinacy is attained by using higher resolution data, for instance down to approximately 4 or 5 Å resolution.

After the parameter K has been chosen, the correlation coefficient between the Fourier amplitudes is calculated from the initial distribution of scattering bodies and the experimental data.

VI. Condensing Protocol

After the initial correlation has been determined, the distribution of scattering bodies is modified to increase the correlation between the calculated amplitudes and the experimental data.

The general strategy used to modify the distribution is to randomly select one of the $N_{hs}$ scattering bodies and randomly move it. The distance and direction of the movement are constrained, however. In a preferred embodiment, the scattering body is moved an initial predetermined distance in a random direction. The predetermined distance is chosen according to the other parameters, such as the asymmetric unit dimensions, the correlation coefficient, number of scattering bodies, etc., and is chosen to allow the scattering bodies to "explore" the asymmetric unit. In other embodiments, scattering bodies each are constrained moved a random distance within a predetermined range. For example, a scattering body may be moved a random distance between zero and one-third the average dimension of the asymmetric unit. In another preferred embodiment, each scattering body is constrained to move parallel to one of the six directions defined by the unit cell edges.

The random movements of the scattering bodies are constrained by the "physical properties" of the spheres: some movements are not allowed. For instance, after a scattering body is moved, it cannot occupy the space as another scattering body (i.e., the surfaces of any two scattering bodies cannot intersect). If this packing constraint is violated, the move is rejected and another scattering body is moved randomly, subject to the same constraint. If the scattering body is moved to a location that is outside of the asymmetric units it is repositioned back into the unit by use of the appropriate space-group dependent symmetry operator (the scattering body is "folded" back into the asymmetric unit). Upon completion of an allowable move, the scattering amplitudes for the new distribution is calculated, and the correlation coefficient is reassessed for this new distribution of scattering bodies. If the correlation coefficient is more favorable (indicating a closer fit), then the move is accepted. Otherwise the move is rejected, and the sphere is returned to its original position. In this way only moves that result in a closer fit are allowed.

In preferred embodiments, a further constraint reflecting the compactness of scatterers is enforced on each move. That is, a move must first satisfy the packing constraint, second alter the correlation coefficient in a favorable manner, and then result in a more "compact" set of scatterers. A move that fails to meet any one of these three criteria is rejected.

Compactness is a measure of how close together the scatterers are as a system and is measured by summing the pairwise interatomic distances for each pair of scatterers. The compactness constraint is satisfied when this sum does not increase substantially for a particular movement in the condensing protocol. The interatomic sum, however, must take into account the symmetry relationships between scatterers in symmetry-related positions. For example, in a crystalline lattice that has two symmetry-related asymmetric units, calculating the distances between two scatterers, S1 and S2, involves determining two separate interatomic distances. The first is the distance between S1 in the first asymmetric unit and S2 also in the first asymmetric unit while the second distance is the distance between S1 in the first asymmetric unit and S2 in the second asymmetric unit. In preferred embodiments, the smallest of the symmetry-related interatomic distances is used to determine compactness. Physically, the consideration of interatomic distances between scatterers in different asymmetric units corresponds to a scatterer moving away from a macromolecular envelope in one asymmetric unit to a position that is closer to the macromolecular envelope in another asymmetric unit.

The compactness constraint preferentially forces the scatterers to move closer together in the condensing procedure and reflects the notion that macromolecules are generally globular and compact structures. Furthermore, enforcement of the compactness constraint forces the scatterers into the macromolecular envelope, or positive image, as discussed in detail below. This constraint will not work for all macromolecules, however. In the rare cases where the subject molecule is not compact or has high amounts of solvent incorporated into the macromolecular envelope, such as, for example tropomyosin which crystallizes as elongated rods having approximately 70% water incorporated in the unit cell, the compactness constraint artificially forces the scatterers to move together resulting in a spurious macromolecular envelope that is erroneously globular in shape.

Use of the compactness constraint in addition to the packing and correlation coefficient constraints results in electron density models having well-defined surfaces—the division of the empty regions and the regions containing scatterers is more pronounced. As discussed in detail in the examples, the j values (a measure of the quality of the model) is higher (approximately 5–10).

A benefit of the well-defined surfaces resulting from application of the compactness constraint is that the input data can be less complete to achieve results similar to the method that applies only the packing and correlation coefficient constraints. For example, when the experimental data is only 80 to 90% complete at low resolution and the compactness constraint is not enforced, the scatterers preferentially move to the solvent, but j and the envelope quality are only fair. If the compactness constraint is applied to the same incomplete data, however, the scatterers preferentially move into the positive image, j and the envelope quality are improved.

This process of moving a scattering body is defined as a "microcycle." A microcycle is "attempted" if the movement of the body is allowed (that is, the "physical" constraint is satisfied) and the correlation coefficient is calculated. Otherwise the microcycle is "rejected." If the correlation coefficient calculated for the new distribution indicates a closer fit between the experimental data and calculated amplitudes, the move is "accepted," and a new microcycle is started. If, however, the correlation coefficient indicates a worse fit, the move is "rejected."

Figure 2:
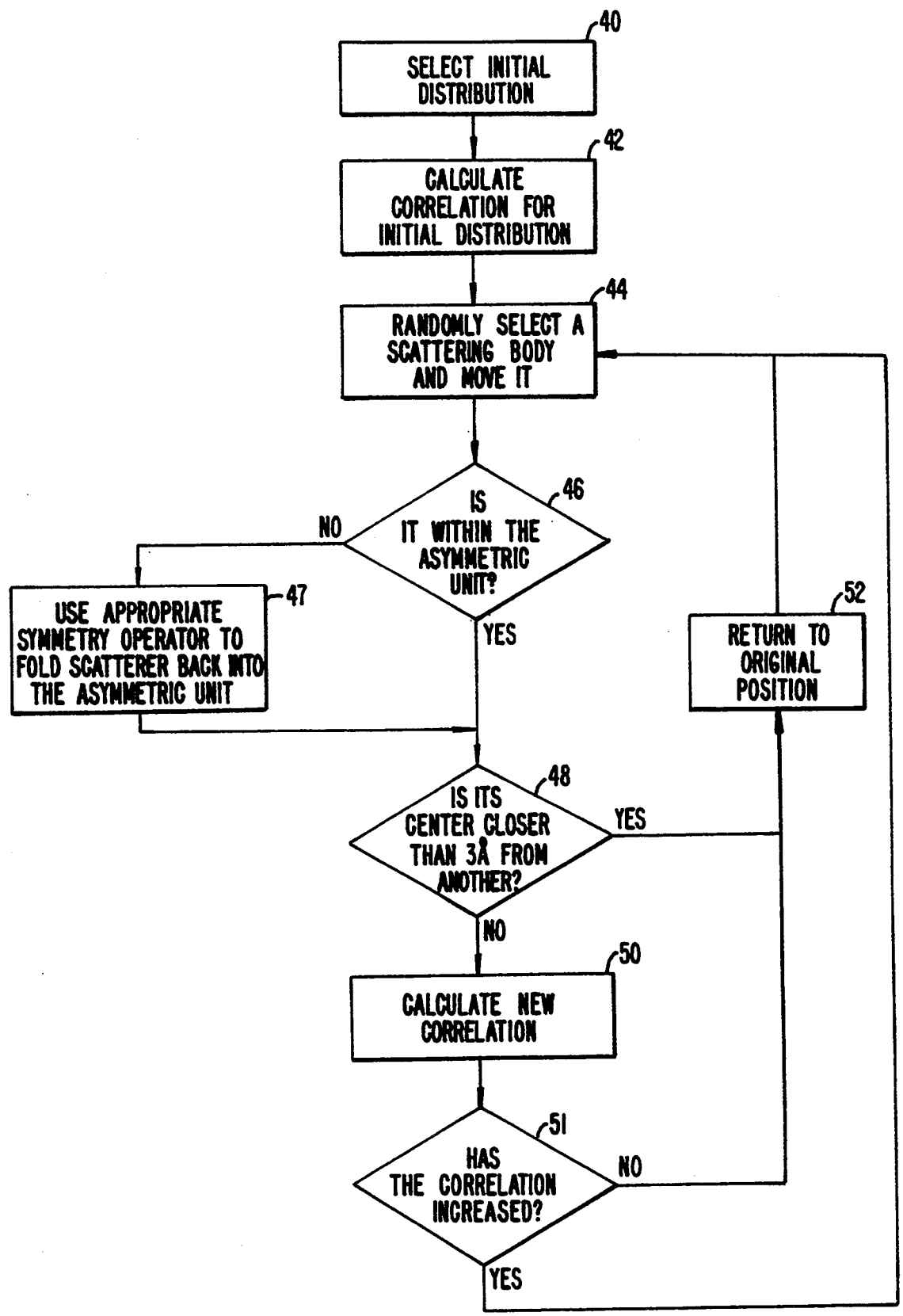
FIG. 2 is a schematic flowchart showing the steps in a microcycle.

Referring now to FIG. 2, the steps involved in each microcycle are shown schematically in a flowchart. After the initial distribution of scatterers is selected 40 and the correlation coefficient, r, is calculated 42, one of the scatterers is randomly selected and moved 44 under the constraints described above. The new position of the scatterer is determined and if it is further than 3 Å away from another scatterer (steps 46 and 48, respectively), and the correlation coefficient is calculated for this new distribution 50. If the movement criterion is violated or r increases (indicating a worse fit), the scattering body is returned to its original position 52, and the microcycle begins again.

After the first microcycle is accepted, another scattering body is randomly selected and moved randomly according to the previously-described constraints. In a preferred embodiment, the scattering bodies are moved by the same predetermined distance, or step-size, x, during each microcycle until the distribution has condensed to a stable state (i.e., when the correlation coefficient has converged to a stable environment that indicates an effective maximum between the correlation between the calculated amplitudes of the scattering bodies and the experimental data). The number of microcycles that are attempted as well as the number of microcycles that result are accepted and rejected are tabulated throughout the condensation process. When 10 accepted moves occur before a total of 100 attempted microcycles have occurred, the collection of attempted moves is collectively defined as a "condensing microcycle," and indicates that the distribution of scattering bodies, as a whole, is converging to a closer fit with the experimental data. If 10 moves have not been accepted before 100 attempted moves, the set of 100 attempted moves is defined as a "condensed macrocycle," which suggests that the distribution is in a stable environment. At this stage, the distribution of the scattering bodies is effectively maximized at the current step-size. That is, further movement of scatterers will probably not increase the correlation between the data. A set of approximately 200 consecutive macrocycles together constitute a "supercycle." In a preferred embodiment, all microcycles within a supercycle have the same step-size (i.e., each scattering body is moved the same distance within a supercycle). A supercycle can have less than 200 macrocycles if 40 condensed macrocycles occur consecutively, which indicates that the distribution has converged to a close fit with the experimental data using the current step-size that the scattering bodies are moved.

Before the next supercycle is started, the step-size, x, is decreased. Thus, consecutive supercycles have a value of x that typically decreases from the initial step-size, $x_i$, to a final step-size, $x_f$. In a preferred embodiment the initial step-size, $x_i$, is between one and one-eighth of the average dimensions of the asymmetric unit. In a more preferred embodiment, the initial step-size is between one-quarter and one-half of the average dimensions of the asymmetric unit. The final step-size, $x_f$, is typically not much smaller than the resolution, K, of the supplied data.

Alternatively, the step-sizes during a supercycle are randomly selected about a mean step size that is fractionally decreased from the initial step size to the final step size rather than by integral angstrom units. The mean step size during a given supercycle $\mu_q$ is related to the mean step size of the previous supercycle $\mu_{q-1}$, according to the following equation:

$$\mu_q = \tfrac{5}{6}\mu_{q-1}$$

which reduces the step-sizes more rapidly than the previous decrements of integral angstrom units.

To compensate for the large step size decreases early in the condensation procedure and to ensure a smooth and continuous decrease, the step size for a particular move during supercycle q, $x_q$, is allowed to randomly vary about the mean step-size for that supercycle, $\mu_q$. Thus during each supercycle, the applied step size, $x_q$, is chosen randomly, with uniform probability, within the range defined by the following equation:

$$5/6\ \mu_q \leq x_q \leq 5/4\ \mu_q$$

where $\mu_q$ is the mean step size during supercycle q. Together, fractionally decreasing the step-sizes and allowing random variation reduces the computer time to model the electron density of the macromolecule. Incidentally, this also leads to a small improvement in the quality of the final envelopes.

These methods of varying the step-sizes are designed to perform large random movements in early supercycles that span the full size of the asymmetric unit, while subsequent smaller moves in later supercycles sample the asymmetric unit and experimental Fourier data more finely. Not unexpectedly, step-sizes smaller than about a third of the data resolution contribute little to the final outcome.

This procedure—from the first supercycle to the last one—is called the "condensing protocol." When the last supercycle is terminated, the calculated data resulting from the final distribution of scattering bodies will be highly correlated with the experimental data. For example, the value of the Pearson Coefficient, r, is typically in the range of 0.6–0.8, as compared with the typical values of r=0 for random starting configurations, and r=1 for an exact fit.

Direct visualization of the final distribution of scattering bodies is optionally performed on a display device using suitable molecular graphics computer software. Suitable display devices include cathode ray tubes or printed output. Methods for displaying the final distribution are well known in the art and include the use of computer graphics software such as FRODO, HYDPA, McIMDAD, MIDAS, MOGLI. Visualization of the final distribution of scattering bodies outlines the shape of the macromolecular envelope and shows low-resolution features. For proteins, structural motifs such as inter-domain clefts and other prominent surface indentations, are typically observed. The computing time for the condensing protocol is modest—many macromolecular problems require roughly on the order of an hour of computer time on a mainframe computer such as a VAX 8550, produced by Digital Equipment Corporation of Maynard, Massachusetts. Other computers are suitable for practicing the invention, the choice of which will be apparent to one skilled in the art, as described above.

Many of the parameters used with the present invention may be varied. For example, in other embodiments of the invention, the numbers of individual microcycles in a macrocycle, or the number of macrocycles in a supercycle are modified. The constraint that must be observed is that the number of microcycles must be sufficient to sample a sufficient number of the allowable moves during the condensing procedure. In other embodiments, the radii of the scattering bodies are modified concurrently with modification of the scheduling of step-sizes and subject to the constraints imposed by the experimental data.

As the condensing protocol proceeds and the scattering bodies condense into stable positions, the refined distribution of homogeneous and featureless scatterers may occupy the macromolecular volume or the solvent void. Using the invention method described herein that enforces only the packing and correlation constraints, scattering bodies preferentially condense into regions of the asymmetric unit occupied by solvent and away from the regions occupied by protein thus modelling the negative image of the electron density. Using this method, however, the scattering bodies occasionally condense into the regions of the unit cell occupied by protein. Not wishing to be bound by speculative theory, it is believed that the condensation preference is determined by the inherent properties of the solvent, relative to that of the macromolecule. However, when in addition to the packing and correlation coefficients, the compactness constraint is enforced, the scattering bodies preferentially move away from the solvent and to regions occupied by the protein.

Except at extremely low resolutions, the solvent void and macromolecular volume have an important difference: the macromolecule is not featureless, in contrast to the solvent void. That is, at most resolutions a macromolecule and, therefore, the associated positive image have internal variations in electron density that are due to the local electron density variation within atoms or event due to small regions of solvent. In contrast, the negative image, which corresponds to the regions of the asymmetric unit occupied by solvent, is essentially featureless since the solvent randomly and uniformly fills these regions. Atoms that lie within the molecular envelope of the protein diffract to give the positive image internal features, while atoms within the solvent space, due to their generally random orientations and locations, do not give a diffraction pattern. Thus, the distribution of scatterers used in this method, which are featureless and homogeneous, models the negative image more readily.

On occasions, however, the scatterers condense to model the positive image. Such solutions occur infrequently, and occur especially when a poor set of parameters is chosen. Thus, an incorrect number of scatterers, a very small initial step size, etc., may contribute to modelling of the positive image. This possibility of mistakenly interpreting a positive image for the negative one can be avoided.

Whether a given final distribution of scattering bodies (i.e., image) is positive or negative is assessed by different methods, such as a suitable density-based refinement. This type of refinement compares the final image with its inverse as a function of changing parameters. For example, the final distribution of condensed scatterers are assigned variable X-ray scattering parameters, such as the scattering cross-section, which are used to calculate a new set of amplitudes for both the image and its inverse. By first calculating the correlation of each set of calculated amplitudes with the experimental data, and comparing the correlations, there is a basis for discrimination, particularly at higher resolutions. The negative image generally has a higher correlation.

Another method for assessing the final distribution incorporates higher resolution experimental data. After the final distribution of scatterers is determined, additional higher resolution data is incorporated into the calculation of the correlation coefficient. Thus, the correlation coefficients between the final distribution and the experimental Fourier coefficients incorporating higher resolution data, and the correlation coefficient between the inverse of final distribution and the same data are calculated. As more of the high resolution data are incorporated into these calculations, one expects that the correlation coefficient of the positive image would indicate a worse fit at a faster rate than the negative image, due to the aforementioned increase in internal structure of the positive image obtained from incorporation of higher resolution data. Modelling of the solvent space is not as sensitive to higher resolution data.

On the other hand, using the invention method described herein that applies the packing, correlation coefficient and the compactness constraints preferentially forces the scattering bodies into the positive image. As discussed above, the compactness constraint forces the system of scatterers to have a smaller total interatomic distance.

In preferred embodiments, the invention method models the electron density of a macromolecule using both sets of constraints. First, the condensing protocol enforces only the packing and correlation coefficient constraints. In the majority of cases, the scatterers condense into the portion of the asymmetric unit filled with solvent. The condensing protocol is run a second time, enforcing the three constraints. When the second condensation produces a macromolecular envelope that is complementary to the one produced by the latter condensation, one is ensured of obtaining an unambiguous model.

Those skilled in the art will recognize that variations of the compactness constraint are possible. For example, in a preferred embodiment, the interatomic sum must decrease for each microcycle. Other variations include using a different metric to evaluate compactness such as, for example, construction of a surface that encloses the majority of the scatterers (i.e., 90%) and using the of volume bound by the surface as the compactness constraint.

In preferred embodiments, the results from the low resolution technique aids in high resolution structure determination in the following cases: (1) traditional molecular replacement with full or partial models; (2) phase extension based on three- or more fold non-crystallographic symmetry; (3) available high-resolution SIR data; (4) two dimensional electron microscopy, where Fourier data are typically of higher resolution than the available direct phases; and (5) verification of suitable heavy atom candidate data sets.

VII. Examples

The following examples illustrate, but in no way limit the invention.

Example 1

Modelling of the electron density of crystallized Elastase from *Pseudomonas aeruginosa*

The method of the invention was applied to model the electron density of the protein, Elastase from *Pseudomonas aeruginosa*. The experimental data collected from previous diffraction studies indicated that 70% of the reflections were collected to a resolution of 2.0 Å and to an accuracy of $R_{sym}$ of 3.5%. Examination of the diffraction data indicated that the protein crystallized in the $P2_12_12_1$ space group having unit cell dimensions of a=124.4 Å, b=51.5 Å and c=44.5 Å. The packing fraction of the protein was estimated to be P=0.6, and because of the symmetry of the $P2_12_12_1$ space group, each unit cell had four symmetry-related solvent voids that together accounted for an estimated 40% of the unit cell volume.

Using the experimental data set for the Elastase protein, the condensing protocol was utilized to model the electron density of the unit cell and determine the shape of the molecular envelope of the protein. The following parameters were used:

Number of alpha carbons, $N_{ca}=298$;
Number of hard sphere scatterers, $N_{ha}=199$;
$N_{ref}$ (number of reflections)=470;
Resolution, K=7 Å;
Initial move size, $x_i=12$ Å; and
Final move size, $x_f=8$ Å.

Figure 3:
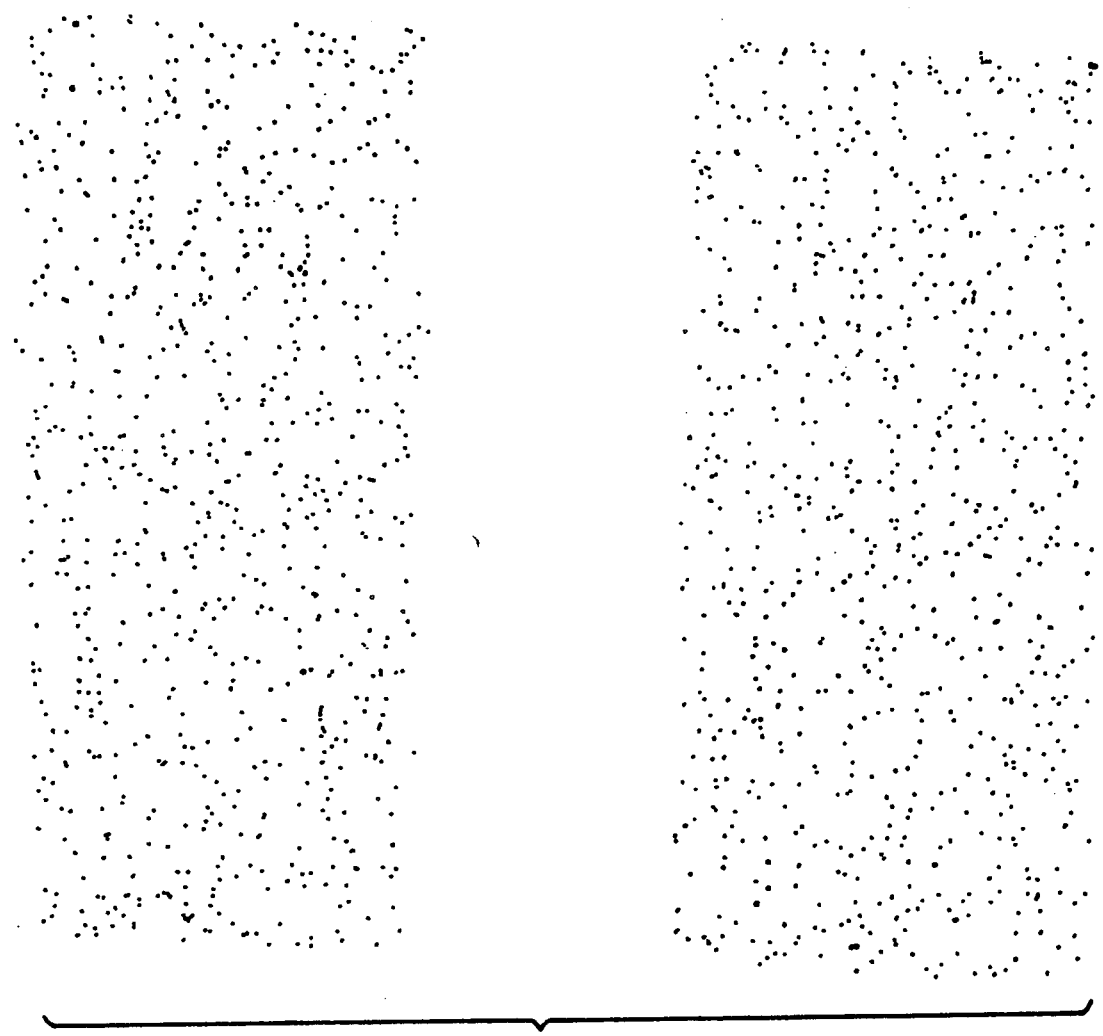
FIG. 3 is a stereoscopic view of an initial random distribution of scattering bodies.

In an initial step, the 199 hard sphere scattering bodies, each having a radius of 1.5 Å, were placed in an initial random distribution by placing a first body in a random location in the unit cell, followed by placing a second body in a random location, and so on, until all 199 bodies had been assigned positions. The only constraint on this process, other than the requirement that each sphere lie fully within the boundaries of the unit cell, was the physical limitation that the outer surfaces of any two spheres not intersect. FIG. 3 shows the initial distribution of scattering bodies. Once the initial distribution was determined, the Fourier amplitudes and phases of hypothetically scattered X-rays were calculated based on the assumption that each sphere, although having a 1.5 Å radius for the purposes of distribution and movement within the unit cell, scattered as if it were a point scatterer. As is known in the art, this calculation is obtained by a trigonometric summation over the positions of the scattering bodies. The Pearson correlation coefficient was calculated from this initial distribution and had an initial value of $r=-0.06$, indicating a poor fit.

Figure 4A:
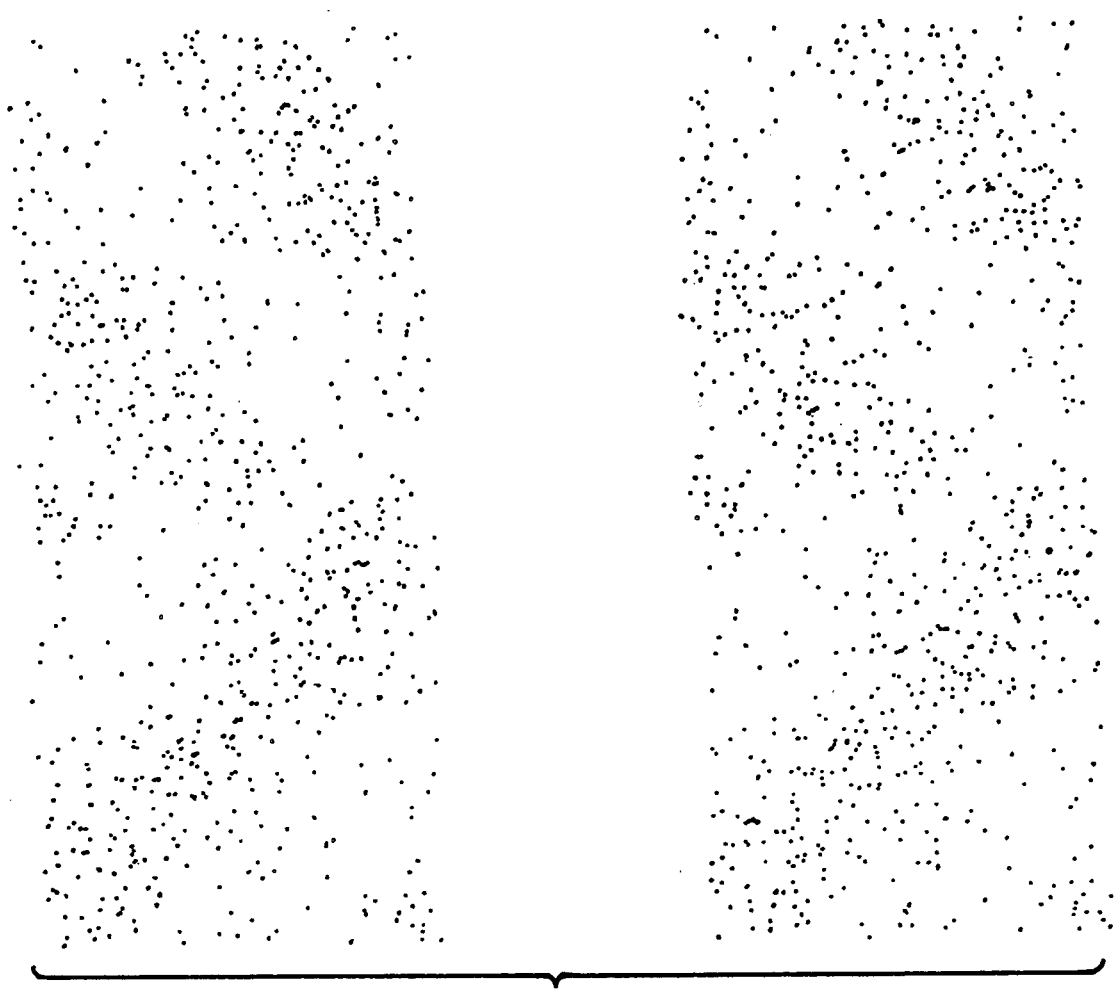
FIG. 4a is a stereoscopic view of the final distribution of scattering bodies after the application of the condensing protocol of the present invention without the compactness constraint.

The condensing protocol, as described above, was utilized to refine the positions of the scattering bodies. After about 40 minutes of computation-time on a VAX 8450 computer, the condensing protocol produced a final configuration of scattering bodies having a Pearson correlation of $r=0.85$. The final distribution of the unit cell, which represents the effectively maximized correlation, is illustrated in FIG. 4a.

The structure of Elastase has previously been solved to a resolution of 2 Å. Comparison of the results obtained from the condensing protocol with the previously solved structure verified the validity of the model. The alpha-carbon backbone of the solved structure was superimposed on the final distribution of scattering bodies, and is presented in FIG. 4b, which clearly shows that the scatterers had preferentially condensed into the solvent void and defined the molecular envelope of the protein, even on the order of 10 Å.

Figure 4B:
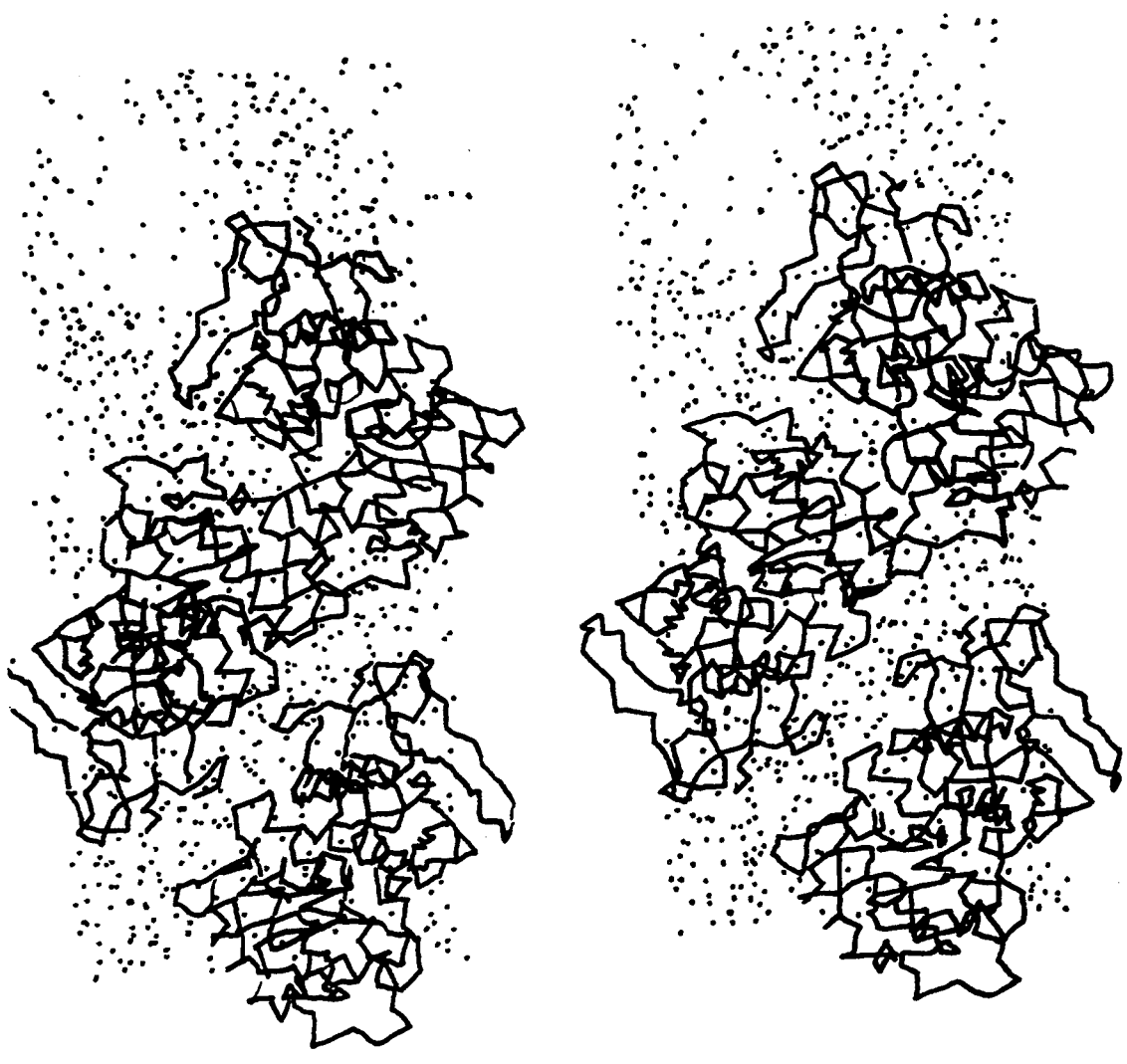
Figure 5A:
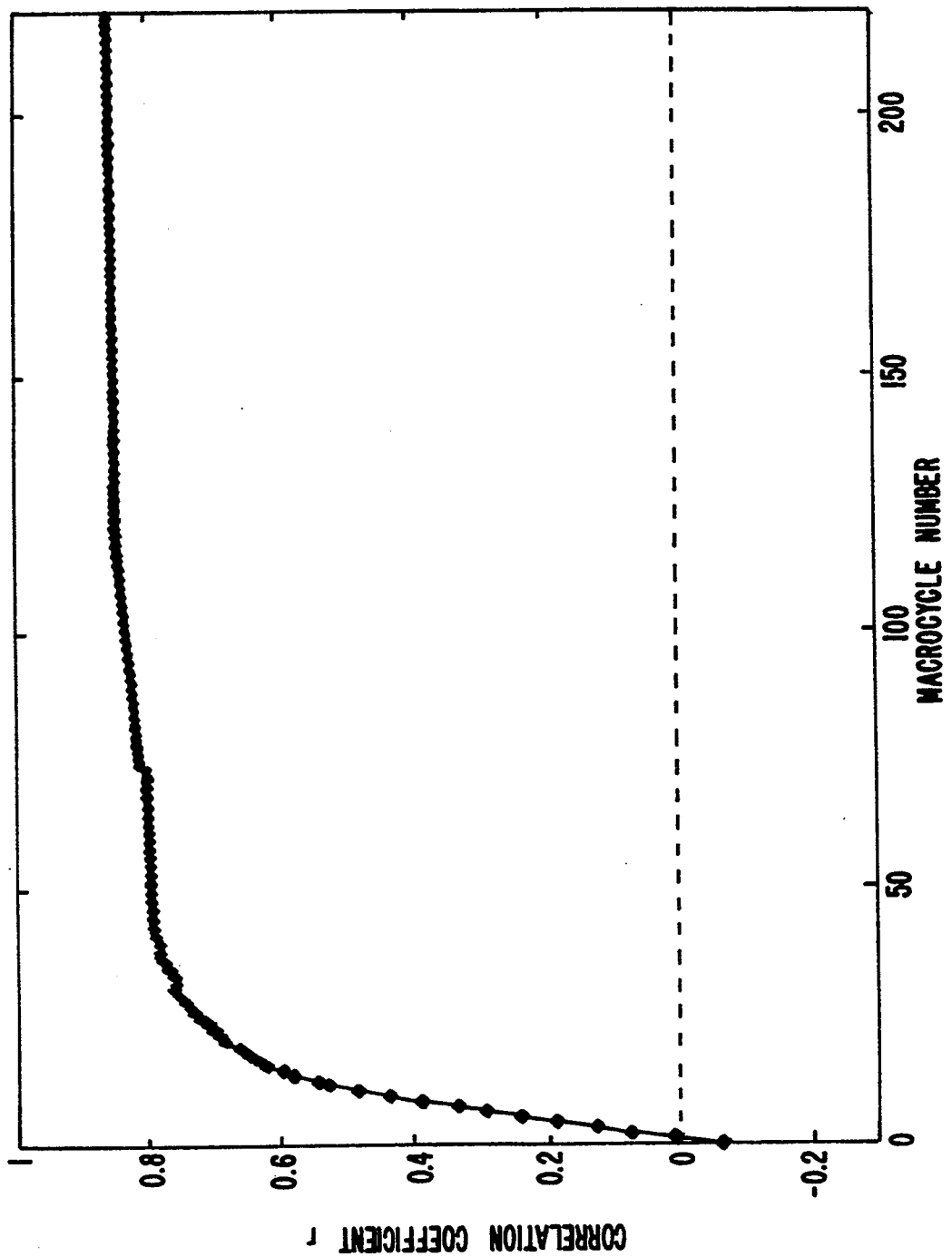
FIG. 5a is a graph showing the behavior of the correlation coefficient, r, during the condensing protocols.
Figure 5B:
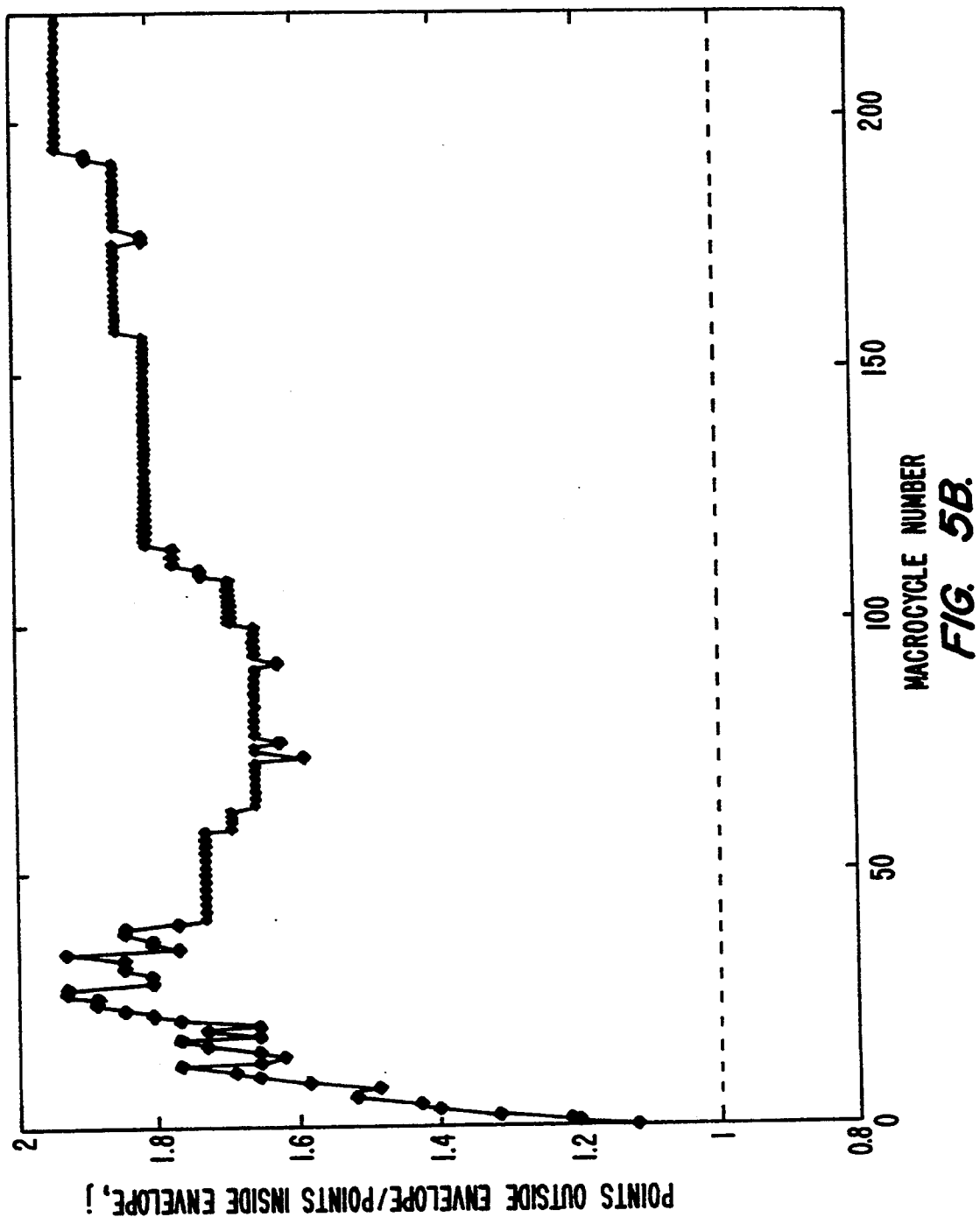
FIG. 5b is a graph showing the behavior of the spatial distribution j, during the condensing protocol.

In order to quantitatively assess the progress of the fit during the condensation procedure, a 10 Å-resolution molecular envelope of the known structure of Elastase was made on a 2 Å grid. The envelope was chosen such that 50% of the grid-points corresponding to the highest electron density were located within the envelope. The accuracy of the model resulting from the condensing protocol was assessed in terms of a spatial distribution ratio, j, which is defined as the number of scattering bodies exterior to this 10 Å resolution envelope, divided by the number interior. For a random distribution of scattering bodies, j is approximately unity, and as condensing protocol proceeds and scatterers move from the interior of the molecular envelope to the exterior, j increases. For analysis purposes, the value of j, as well as the Pearson correlation coefficient, r, were tabulated and plotted as shown in FIGS. 5a–b, for each macrocycle of the condensation protocol. FIG. 5b shows that j increased to 1.93, while the correlation coefficient concurrently increased to 0.85 during the protocol. While this simple measure, j, approximately discriminates between solvent and macromolecule, it does not measure the spatial distribution of scattering bodies within either the solvent void or, more importantly, within the macromolecular envelope. In particular, FIG. 4b shows that the scattering bodies lying within the macromolecular envelope are preferentially distributed toward the macromolecular surface rather than clustered about the molecular centroid.

Figure 6:
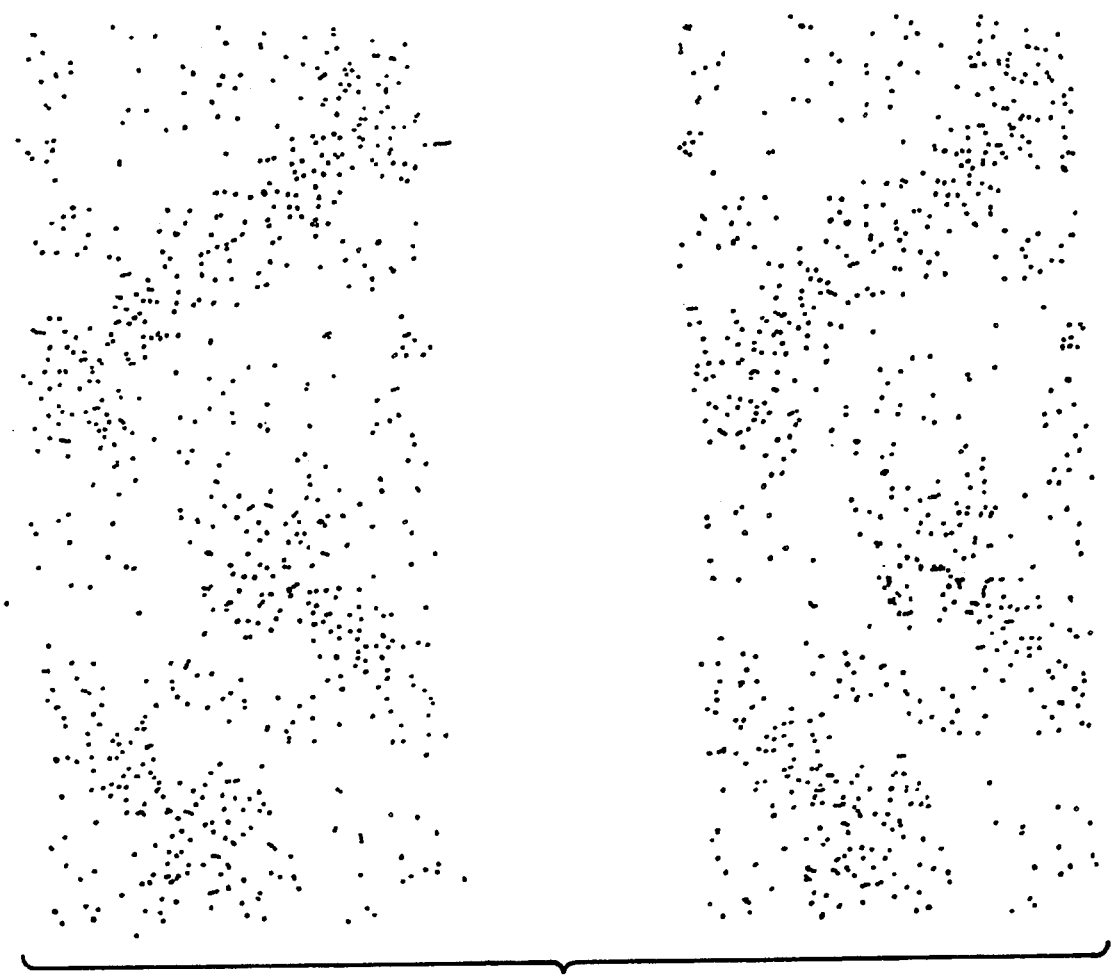
FIG. 6 is a stereoscopic view of the final distribution of scattering bodies obtained for the Elastase used in FIGS. 4a and 4b, but with a different initial distribution of scattering bodies and slightly different parameters.

Finally, to determine whether the final distribution was a relatively unstable local maximum of the correlation function, a different random starting configuration and a different resolution range was used. The following parameters were used:
Number of alpha carbons, $N_{ca}=298$;
Number of hard sphere scatterers, $N_{ha}=199$;
$N_{ref}$ (number of reflections) = 2195;
Resolution, K=4 Å;
Initial move size, $x_i=11$ Å; and
Final move size, $x_f=2$ Å.
The results are shown in FIG. 6.

Since more reflection data were used (as required by the resolution range used in this case), the computer processing time increased to 3.5 hours. The molecular envelope obtained with these parameters was sufficiently detailed to place the alpha carbon model of the protein within a few angstroms of its true center of mass. A limited translational and rotational R-factor search, as is known in the art of molecular replacement, identified the exact location of the molecule within the unit cell.

Example 2

Modelling of the electron density of a crystallized Elastase from *Pseudomonas aeruginosa*

The method of the invention was applied to model the electron density of the protein from Example 1 but included the application of the compactness constraint. Using the experimental data set for the Elastase protein, the condensing protocol was utilized to model the electron density of the unit cell and determine the shape of the molecular envelope of the protein. Exactly as in Example 1, the following parameters were used:
Number of alpha carbons, $N_{ca}=298$;
Number of hard sphere scatterers, $N_{ha}=199$;
$N_{ref}=470$;
Resolution, K=40 to 7 Å;
Initial move size, $x_i=12$ Å; and
Final move size, $x_f=8$ Å.

In an initial step, the 199 hard sphere scattering bodies, each having a radius of 1.5 Å, were placed in an initial random distribution by placing a first body in a random location in the unit cell, followed by placing a second body in a random location, and so on, until all 199 bodies had been assigned positions. The physical constraint on this process, other than the requirement that each sphere lie fully within the boundaries of the unit cell, was the physical limitation that the outer surfaces of any two spheres not intersect. Once the initial distribution was determined, the Fourier amplitudes and phases of hypothetically scattered X-rays were calculated based on the assumption that each sphere, although having a 1.5 Å radius for the purposes of distribution and movement within the unit cell, scattered as if it were a point scatterer. As is known in the art, this calculation is obtained by a trigonometric summation over the positions of the scattering bodies. The Pearson correlation coefficient was calculated from this initial distribution and had an initial value of $r=-0.06$, indicating a poor fit.

Figure 7A:
FIG. 7a is a view of the final distribution of scattering bodies after the application of the condensing protocol of the present invention without the compactness constraint.
Figure 7B:
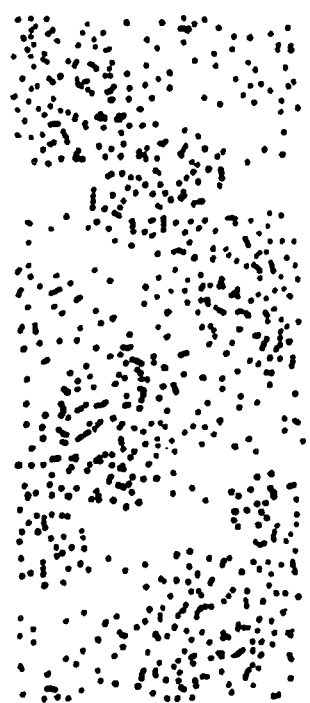
FIG. 7b is a view of the final distribution of scattering bodies after the application of the condensing protocol of the present invention with the compactness constraint.

The condensing protocol including the compactness constraint, as described above, was utilized to refine the positions of the scattering bodies. After about 40 minutes of computation time on a VAX 8450 computer, the condensing protocol produced the final configuration of scattering bodies illustrated in FIG. 7b. In contrast, FIG. 7a shows the final distribution of scattering bodies from example 1. FIG. 7a and 7b are complements of each other-that is, scattering bodies of FIG. 7b lie in the regions of the unit cell that are empty in FIG. 7a. As discussed above in Example 1, the scattering bodies shown in FIG. 7a represent the negative image corresponding to the solvent, and, therefore, the scattering bodies shown in FIG. 7b represent the positive image corresponding to the macromolecule.

Example 3

Modelling of the electron density of a crystallized DNA binding domain of the repressor protein from the 434 phage, Rlt69.

The experimental diffraction data, collected to 1.9 Å with an $R_{sym}$ of 5.4%, indicated that the protein crystallized in the $P2_12_12_1$ space group with unit cell dimensions of a=32 Å, b=37.5 Å, and c=44.6 Å. The packing fraction of the protein was assumed to be P=0.6.

The crystal structure had been previously solved with a refined r-factor of 19%.

The parameters used in this example were:
Number of alpha carbons, $N_{ca}$=63;
Number of hard sphere scatterers, $N_{ha}$ =43;
$N_{ref}$ (number of reflections)=291;
Resolution, K=5 Å;
Initial move size, $x_i$=8 Å; and
Final move size, $x_f$=3 Å.

Because of the small size of the unit cell, higher resolution data was required to have sufficient over-determinacy. Furthermore, since the scattering bodies were not as numerous as in the previous examples and since the unit cell is small, all allowable moves could be sampled using fewer macrocycles. The minimum number of macrocycles per supercycle, therefore, was decreased from 40 to 20, which required less computer processing time. The correlation coefficient for the initial distribution was r=−0.1, and the initial value of j was 0.87. The index of spatial distribution, j, was calculated as described above but using a 6 Å envelope of the Rlt69 model, made on a 2 Å grid.

Figure 8:
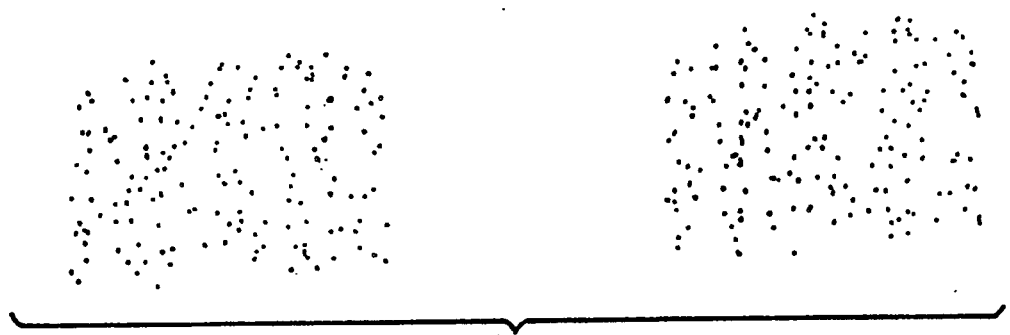
FIG. 8 is a stereoscopic view of an initial distribution of scattering bodies used in modeling the electron density of the Rlt69 fragment of the bacteriophage 434 repressor protein.
Figure 9:
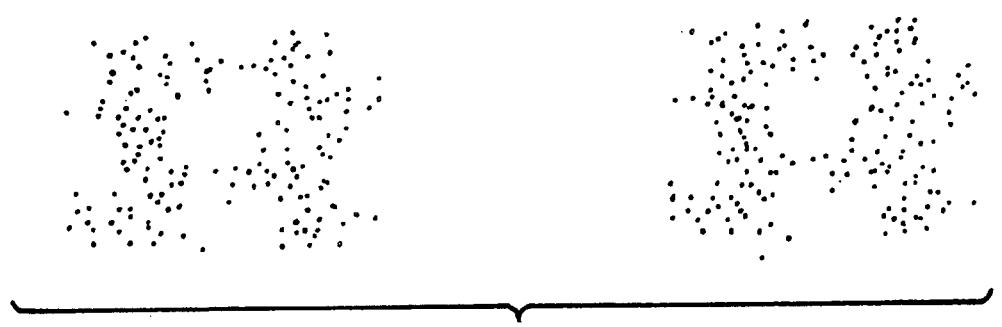
FIG. 9 is a stereoscopic view of the final distribution of scattering bodies after application of the condensing protocol without the compactness constraint.
Figure 10:
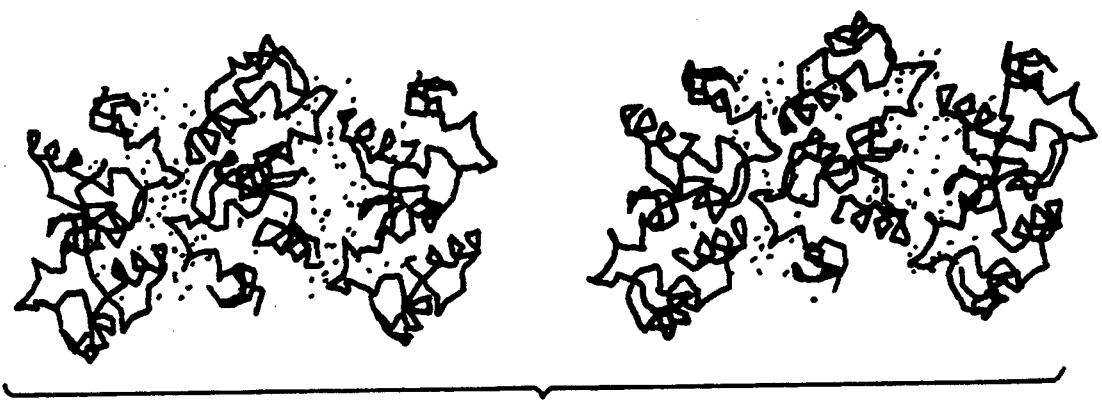
FIG. 10 is a stereoscopic view of the alpha carbon backbone of the protein superimposed on the final distribution of scattering bodies of FIG. 9.
Figure 14:
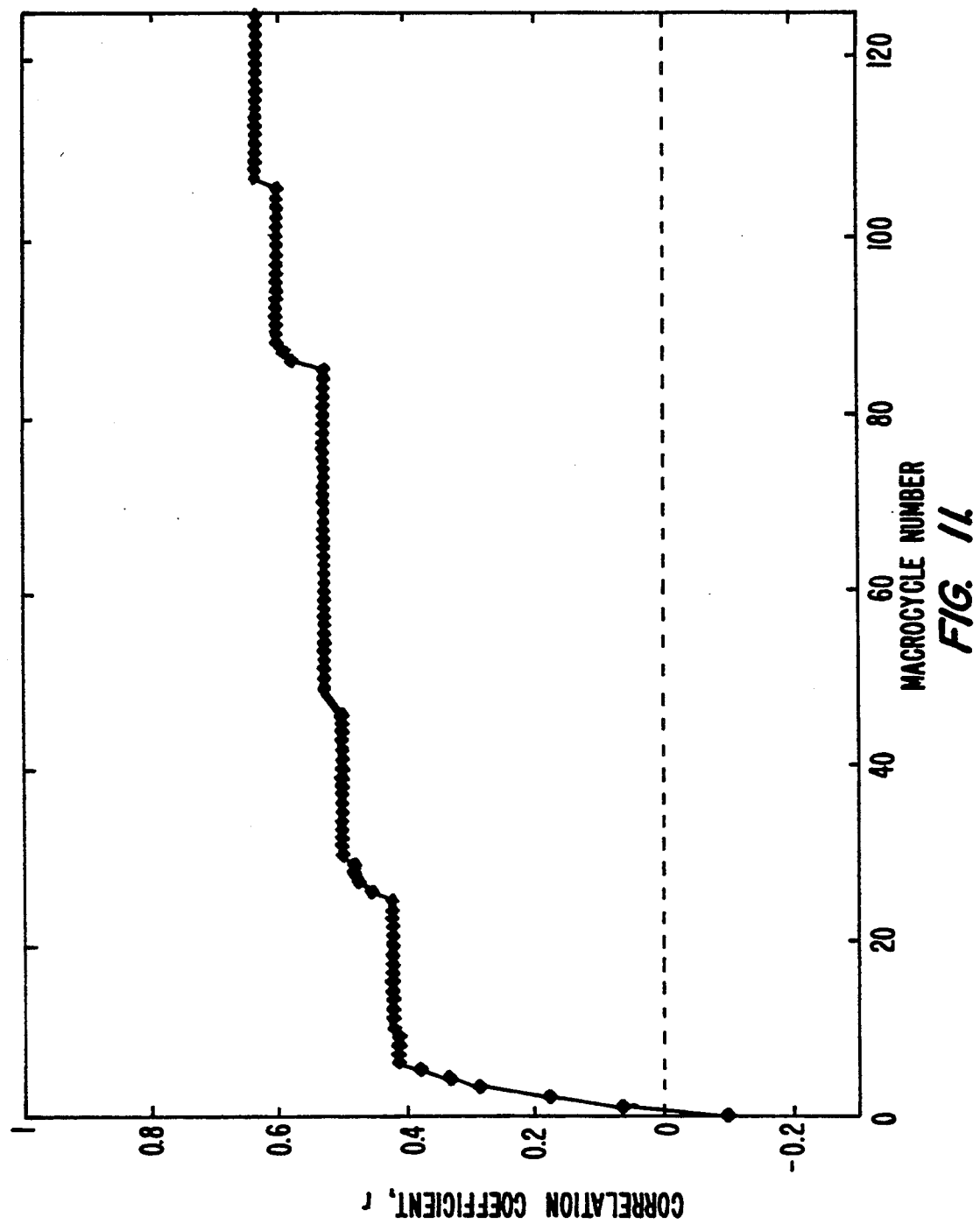
Figure 12:
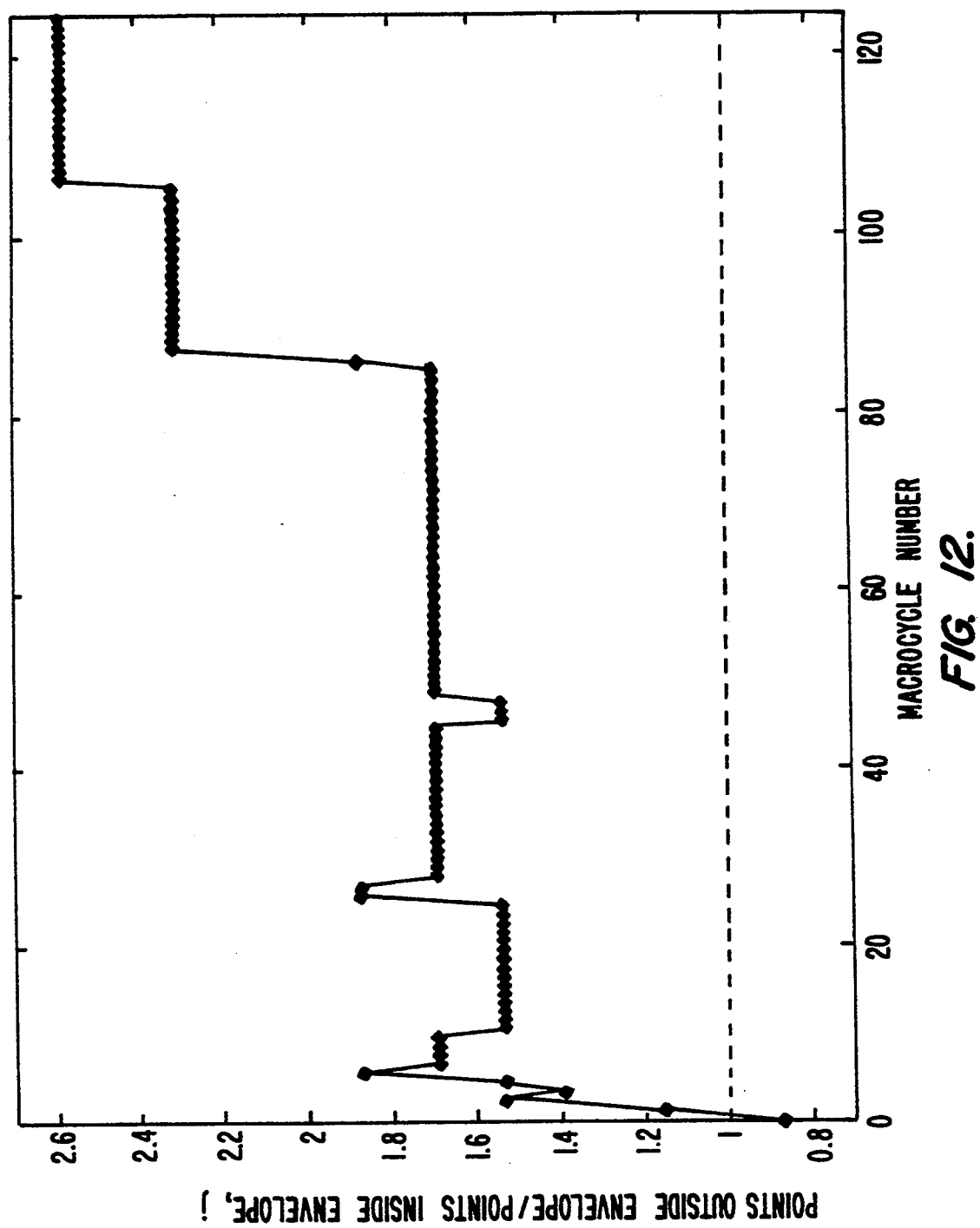
FIG. 12 is a graph showing behavior of the spatial distribution, j, during the condensing protocol of the present invention.

After about 10 minutes of computer processing time, the condensing protocol produced a final distribution of scattering bodies having an effectively maximized correlation of r=0.65 and a j=2.6. FIGS. 8-10 show the initial distribution of scattering bodies, the final distribution of scattering bodies, and the alpha-carbon backbone of the protein superimposed on the final distribution, respectively. FIG. 11 and FIG. 12 show the behavior of r and j during the condensation protocol.

VIII. Other embodiments

Other embodiments are embraced within the present invention. For instance, substantially any crystalline molecule having uniformly diffracting voids within the unit cell can be modeled by the methods described herein. Examples include the modelling of the electron density of polymeric nucleic acids, such as DNA or RNA fragments, as well as nucleic acid-peptide complexes, virus particles and the like.

Other methods for maximizing the correlation between the experimental data and the calculated amplitudes include the downhill simplex method, direction-set methods (such as Powell's method), conjugate gradient methods (such as the Fletcher-Reeves and Polak-Ribiere algorithms), variable metric methods (such as the Davidon-Fletcher-Powell algorithm), simulated annealing, random-walks, and the like. Other methods that maximizes a correlation between the calculated amplitudes and the experimental data can be used.

Moreover, beyond the phaseless Fourier inversion problem of the present invention, other problems can be reformulated in a manner analogous to that presented above. Such as the determination of three dimensional structures using electron microcopy. In another preferred embodiment, the selection of the point scatterers to be moved is not random. For example, the selected point scatterer is the one having the largest increase in the correlation between the changed distribution and the experimental data. In another preferred embodiment, the selected point scatterer is not moved in a random direction, but in a direction corresponding to a predetermined algorithm. For example, the direction is selected to effectively maximize the increase of the correlation between the distribution and the experimental data.

Moreover, in other embodiments, a plurality of point scatterers are simultaneously moved in one cycle. The number of point scatterers that are moved simultaneously is between one and all of the point scatterers present. In other embodiments, the distance that a point scatterer is moved in a cycle is variable. That is, the distance moved is not a fixed, pre-determined distance. In a preferred embodiment, the move distance is randomly chosen, but constrained in a predetermined range. Alternatively, the correlation coefficient versus the move distance is calculated, and the scatterer is moved to maximize the correlation. Rather it is varied dynamically in a manner that is consistent with the other aforementioned standard maximization methods. However, the move distances cannot be far different from the appropriate pre-determined distances that are characterized.

The present invention provides new methods for modelling the electron density of a macromolecule in a crystal lattice. It is to be understood that the above description is intended to be illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for modelling the electron density distribution of a macromolecule in a defined asymmetric unit of a crystal lattice having locations of uniformly diffracting electron density, comprising:
    (a) inputing data collected from an X-ray diffraction experiment into the computer;
    (b) converting a portion of the data into normalized amplitudes;
    (c) producing an initial distribution of scattering bodies within a asymmetric unit having the same dimensions as the defined asymmetric unit;
    (d) calculating scattering amplitudes of said initial distribution and determining a correlation between the calculated scattering amplitudes and said normalized amplitudes;
    (e) moving at least one of said scattering bodies within the asymmetric unit to create a modified distribution;
    (f) calculating scattering amplitudes and phases of said modified distribution and determining the correlation between said calculated amplitudes and said normalized values; and (g) producing a final distribution of scattering bodies by repeating steps e) and f) until the correlation between said calculated scattering amplitudes and said normalized amplitudes is maximized, said final distribution of scattering bodies defining the electron density of the crystal.

2. The method of claim 1 wherein each of said moved scattering bodies is moved a predetermined distance.

3. The method of claim 2 further comprising the step of refining said final distribution of scattering bodies, said refining step comprising:

(a) reducing said predetermined distance;

(b) moving at least one of said scattering bodies by said reduced distance within the asymmetric unit to modify said distribution;

(c) calculating scattering amplitudes and phases of said modified distribution and determining the correlation between said calculated amplitudes and said normalized amplitudes; and (d) producing a final distribution of scattering bodies by repeating steps (b) and (c) until the correlation between calculated amplitudes of said distribution and said normalized valued is maximized, said final distribution of scattering bodies defining a refined electron density of the crystal.

4. The method of claim 3 wherein said refining step is repeated until said distance is reduced to a predetermined final distance.

5. The method of claim 4 wherein said scattering bodies are translated in a random translation direction.

6. The method of claim 5 wherein the random translation direction is selected randomly from predefined translation directions.

7. The method of claim 6 wherein said predefined directions are parallel to the axes defined by the crystal lattice asymmetric unit.

8. The method of claim 4 wherein said steps of determining the correlation between said calculated amplitudes of scattering bodies and said normalized amplitude comprises calculating a correlation coefficient between said calculated amplitudes and said normalized values.

9. The method of claim 8 wherein said correlation coefficient is the Pearson coefficient.

10. The method of claim 9 wherein said steps of maximizing the fit between the calculated amplitudes and the normalized amplitudes comprise maximizing said Pearson coefficient.

11. The method of claim 8 wherein said correlation coefficient comprises a R-value.

12. The method of claim 11 wherein said steps of maximizing the fit between the calculated amplitudes and the normalized amplitudes comprise minimizing said R-value.

13. The method of claim 4 wherein said scattering bodies are spherical and the centers of any two said spherical scattering bodies are separated by at least a distance equal to the sum of their respective radii.

14. The method of claim 13 wherein each of said scattering bodies is placed in a random position in said asymmetric unit to create said initial distribution.

15. The method of claim 13 wherein each of said scattering bodies is placed in a regular position in said asymmetric unit.

16. The method of claim 4 wherein the locations occupied by said scattering bodies in said final distribution defines uniformly scattering electron density, and the unoccupied space defines electron density of the macromolecule in the crystal lattice.

17. The method of claim 4 wherein said normalized amplitudes comprise normalized E-values.

18. The method of claim 4 wherein said normalized amplitudes comprise normalized F-values.

19. The method of claim 1 wherein the step of moving at least one of said scattering bodies is conducted such that the total distance between the scattering bodies is not increased.

20. The method of claim 19 wherein said final distribution of scattering bodies preferentially represents the portion of the asymmetric unit occupied by the macromolecule.

21. In a digital computer, a method for modelling the electron density distribution of a macromolecule in a defined asymmetric unit of a crystal lattice having locations of uniformly diffracting electron density, comprising:

inputting experimental data collected from an X-ray diffraction experiment into the computer;

randomly distributing a plurality of scattering bodies in an asymmetric unit having substantially the same dimensions as the defined symmetric unit; and repeatedly moving said plurality of scattering bodies to more compact distributions such that the total distance between scattering bodies is decreasing, and determining scattering amplitudes of the scattering bodies in each distribution until reaching a final distribution of scattering bodies, the final distribution having scattering amplitudes having a maximum fit with amplitudes from said experimental data, said final distribution also defining the electron density distribution of the macromolecule in the defined asymmetric unit.

22. The method of claim 21 wherein the step of repeatedly moving said plurality of scattering bodies to more compact distributions includes the steps of summing the pairwise distances of the scattering bodies of a proposed move of the scattering bodies; and accepting the move if the sum of the pairwise distances does not increase by more than predefined amount from a sum determined for the previous distribution.

23. A method for modelling the electron density distribution of a molecule within asymmetric unit of a crystal lattice, said molecule occupying a said portion of said asymmetric unit and solvent occupying the remaining portion of said asymmetric unit, the method comprising:

producing an initial distribution of spherical scattering bodies each having a predetermined radius with an asymmetric unit having the same dimensions as the asymmetric unit of the crystal, the initial distribution having a defined total distance between the scattering bodies; and transforming said initial distribution of scattering bodies into a final distribution of scattering bodies by repeatedly moving the scattering bodies to new distributions having less total distance between scattering bodies, said scattering bodies of said final distribution representing the portion of the asymmetric unit occupied by solvent.

24. A method for modelling the electron density distribution of a macromolecule in an asymmetric unit of a crystal lattice by X-ray crystallography comprising:

(a) irradiating the crystal lattice with X-rays and recording experimental X-rays and recording experimental X-ray diffraction data;

(b) determining the dimensions of a asymmetric unit of said crystal from said diffraction data;

(c) producing an initial distribution of a plurality of spherical scattering bodies by placing each of said scattering bodies within an asymmetric unit having the same dimensions as the asymmetric unit of the crystal lattice, each of said spherical scattering bodies have a predetermined radius;

(d) calculating scattering amplitudes of said initial distribution of scattering bodies;

(e) determining the fit between the calculated amplitudes of said distribution and said experimental data;

(f) translating at least one of said scattering bodies within the asymmetric unit to modify said distribution;

(g) calculating scattering amplitudes and phases of said modified distribution of scattering bodies;

(h) determining the fit between said calculated amplitudes of said modified distribution and said normalized experimental data; and (i) producing a final distribution of scattering bodies repeating steps (f) through (h) until the fit between said distribution of scattering bodies and said experimental data is effectively maximized, said final distribution of scattering bodies being an electron density model of said crystal.

* * * * *